(12) United States Patent
Shirihai et al.

(10) Patent No.: US 10,925,975 B2
(45) Date of Patent: Feb. 23, 2021

(54) ACIDIC NANOPARTICLES FOR RESTORATION OF AUTOPHAGY

(71) Applicants: THE REGENTS OF THE UNIVERSITY OF CALIFORNIA, Oakland, CA (US); The Trustees of Boston University, Boston, MA (US)

(72) Inventors: Orian Shirihai, Los Angeles, CA (US); Mark Grinstaff, Brookline, MA (US); Jialiu Zeng, Singapore (SG)

(73) Assignees: THE REGENTS OF THE UNIVERSITY OF CALIFORNIA, Oakland, CA (US); TRUSTEES OF BOSTON UNIVERSITY, Boston, MA (US)

( * ) Notice: Subject to any disclaimer, the term of this patent is extended or adjusted under 35 U.S.C. 154(b) by 29 days.

(21) Appl. No.: 16/252,927

(22) Filed: Jan. 21, 2019

(65) Prior Publication Data
US 2019/0224336 A1 Jul. 25, 2019

Related U.S. Application Data

(60) Provisional application No. 62/619,565, filed on Jan. 19, 2018.

(51) Int. Cl.
*A61K 47/69* (2017.01)
*A61P 3/04* (2006.01)
(Continued)

(52) U.S. Cl.
CPC .......... *A61K 47/6935* (2017.08); *A61K 47/55* (2017.08); *A61P 3/04* (2018.01); *A61P 3/10* (2018.01); *A61P 25/28* (2018.01); *A61K 9/0019* (2013.01); *A61K 9/0053* (2013.01); *B82Y 5/00* (2013.01)

(58) Field of Classification Search
CPC ................................................. A61K 47/6935
See application file for complete search history.

(56) References Cited

U.S. PATENT DOCUMENTS

| 2,539,438 A | 1/1951 | Kropa et al. |
| 5,512,651 A | 4/1996 | Carlson et al. |

(Continued)

FOREIGN PATENT DOCUMENTS

WO   WO 2017/062920   4/2017

OTHER PUBLICATIONS

Antheunis et al., "Autocatalytic Equation Describing the Change in Molecular Weight during Hydrolytic Degradation of Aliphatic Polyesters", Biomacromolecules, Feb. 2010, 11(4): 1118-1124.
(Continued)

*Primary Examiner* — Benjamin J Packard
(74) *Attorney, Agent, or Firm* — Mark S. Cohen; Pearl Cohen Zedek Latzer Baratz LLP

(57) ABSTRACT

In various embodiments novel biodegradable acid-activated acid releasing nanoparticles (acNPs) are provided that are used as a targeted strategy to manipulate lysosomal acidity and autophagy. These acNPs based, in certain embodiments, on fluorinated polyesters are degraded at pH 6.0 (pH reported in dysfunctional lysosomes), and release component acids that further lower the lysosomal pH, and thereby increasing autophagic flux and cellular function of hepatocytes under LT. The acNPs can serve as a therapeutic in restoring liver-diseases.

47 Claims, 32 Drawing Sheets

(51) Int. Cl.
  A61P 3/10    (2006.01)
  A61P 25/28   (2006.01)
  A61K 47/55   (2017.01)
  B82Y 5/00    (2011.01)
  A61K 9/00    (2006.01)

(56) References Cited

U.S. PATENT DOCUMENTS

2006/0223785 A1  10/2006  Liu et al.
2012/0086761 A1   4/2012  Chrítien et al.
2016/0367489 A1  12/2016  Chiu et al.

OTHER PUBLICATIONS

Khambu et al., "Autophagy in non-alcoholic fatty liver disease and alcoholic liver disease", Liver Research, 2 (2018) 112-119.
Lam et al., "Treatment options for nonalcoholic fatty liver disease", Therapeutic Advances in Gastroenterology, 2010, 3(2): 121-137.
Von Burkersroda et al., "Why degradable polymers undergo surface erosion or bulk erosion", Biomaterials, Nov. 2002, 23(21): 4221-4231.
Ahmed, "Non-alcoholic fatty liver disease in 2015", World Journal of Hepatology, Jun. 18, 2015, 7(11): 1450-1459.
Ashtari et al., "Non-alcohol fatty liver disease in Asia: Prevention and planning", World Journal of Hepatology, Jul. 8, 2015, 7(13): 1788-1796.
Bril et al., "Hepatic Steatosis and Insulin Resistance, But Not Steatohepatitis, Promote Atherogenic Dyslipidemia in NAFLD", J. Clin. Endocrinol. Metab., Feb. 2016, 101(2): 644-652.
Alkhouri et al., "Lipotoxicity in Nonalcoholic Fatty Liver Disease: Not All Lipids Are Created Equal", Expert Rev. Gastroenterol. Hepatol., Aug. 2009, 3(4): 445-451.
Mei et al., "Differential Roles of Unsaturated and Saturated Fatty Acids on Autophagy and Apoptosis in Hepatocytes", The Journal of Pharmacology and Experimental Therapeutics, 2011, 339(2): 487-498.
Terman et al., "Mitochondrial Turnover and Aging of Long-Lived Postmitotic Cells: The Mitochondrial-Lysosomal Axis Theory of Aging", Antioxidants & Redox Signaling, 2010, 12(4): 503-535.
Kwanten et al., "Role of autophagy in the pathophysiology of nonalcoholic fatty liver disease: A controversial issue", World J. Gastroenterol., Jun. 21, 2014, 20(23): 7325-7338.
Lavallard et al., "Autophagy and Non-Alcoholic Fatty Liver Disease", BioMed Research International, vol. 2014, (Sep. 10, 2014), Article ID 120179, 13 pages.
Fukuo et al., "Abnormality of autophagic function and cathepsin expression in the liver from patients with non-alcoholic fatty liver disease", Hepatology Research, 2014, 44: 1026-1036.
Inami et al., "Hepatic steatosis inhibits autophagic proteolysis via impairment of autophagosomal acidification and cathepsin expression", Biochem. Biophys. Res. Commun., 2011, 412, pp. 618-625.
Vidal-Donet et al., "Alterations in ROS Activity and Lysosomal pH Account for Distinct Patterns of Macroautophagy in LINCL and JNCL Fibroblasts", PLoS One, Feb. 2013, 8(2): e55526, 13 pages.
Kawai et al., "Autophagosome-Lysosome Fusion Depends on the pH in Acidic Compartments in CHO Cells", Autophagy, Mar./Apr. 2007, 3(2): 154-157.
Yamamoto et al., "Bafilomycin A1 Prevents Maturation of Autophagic Vacuoles by Inhibiting Fusion between Autophagosomes and Lysosomes in Rat Hepatoma Cell Line, H-4-II-E Cells", Cell Structure and Function, 23: 33-42 (1998).
Holopainen et al., "Elevated lysosomal pH in neuronal ceroid lipofuscinoses (NCLs)", Eur. J. Biochem. 268, 2001, pp. 5851-5856.
Las et al., "Fatty Acids Suppress Autophagic Turnover in β-Cells", The Journal of Biological Chemistry, 286(49): 42534-42544, Dec. 9, 2011.
Schneider et al., "Autophagy and human disease: emerging themes", Curr. Opin. Genet. Dev., Jun. 2014, pp. 16-23.
Kroemer, "Autophagy: a druggable process that is deregulated in aging and human disease", The Journal of Clinical Investigation, 125(1): Jan. 1-4, 2015.
Dutta et al., "Upregulated autophagy protects cardiomyocytes from oxidative stress-induced toxicity", Autophagy, 9(3): 328-344, Mar. 2013.
Boustany, "Lysosomal storage diseases—the horizon expands", Nature Reviews Neurology, Aug. 13, 2013, pp. 1-16.
González-Rodríguez et al., "Impaired autophagic flux is associated with increased endoplasmic reticulum stress during the development of NAFLD", Cell Death and Disease, 2014, 5, e1179, 13 pages.
Park et al., "Calcium channel blockers as potential therapeutics for obesity-associated autophagy defects and fatty liver pathologies", Autophagy, 10(12): 2385-2386, Dec. 2014.
Chitturi, "Treatment options for nonalcoholic fatty liver disease", Therapeutic Advances in Gastroenterology, 2008, 1(3): 173-189.
Liu et al., "Effective treatment of steatosis and steatohepatitis by fibroblast growth factor 1 in mouse models of nonalcoholic fatty liver disease", Proc. Natl. Acad. Sci., Feb. 23, 2016, 113(8): 2288-2293.
Portillo-Sanchez et al., "Treatment of Nonalcoholic Fatty Liver Disease (NAFLD) in patients with Type 2 Diabetes Mellitus", Clinical Diabetes and Endocrinology, 2016, 2(9): 1-9.
Tolman et al., "Treatment of non-alcoholic fatty liver disease", Therapeutics and Clinical Risk Management, 2007, 3(6): 1153-1163.
Chang et al., "Role of thiazolidinediones, insulin sensitizers, in non-alcoholic fatty liver disease", Journal of Diabetes Investigation, 4(6): 517-524, Nov. 2013.
Hardy et al., "Nonalcoholic fatty liver disease: new treatments", Curr. Opin. Gastroenterol., 31(3): 175-183, May 2015.
Galluzzi et al., "Metabolic Control of Autophagy", Cell, Dec. 4, 2014,159(6): 1263-1276.
Rubinsztein et al., "Autophagy modulation as a potential therapeutic target for diverse diseases", Nat. Rev. Drug Discov., Sep. 2012, 11(9): 709-730.
Baratta et al., "Reduced Lysosomal Acid Lipase Activity in Adult Patients With Nonalcoholic Fatty Liver Disease", EBioMedicine 2, (2015) pp. 750-754.
Turk et al., "Lysosomes as 'Suicide Bags' in Cell Death: Myth or Reality?", Journal of Biological Chemistry, Aug. 14, 2009, 284(33): 21783-21787.
Trudeau et al., "Lysosome acidification by photoactivated nanoparticles restores autophagy under lipotoxicity", J. Cell Biol., 214(1): 25-34, 2016.
Baltazar et al., "Acidic Nanoparticles Are Trafficked to Lysosomes and Restore an Acidic Lysosomal pH and Degradative Function to Compromised ARPE-19 Cells", PLoS One, Dec. 2012, 7(12): e49635, 10 pages.
Lee et al., "Lysosomal Proteolysis and Autophagy Require Presenilin 1 and Are Disrupted by Alzheimer-Related PS1 Mutations", Cell, Jun. 25, 2010, 141(7): 1146-1158.
Zhang et al., "Size-Dependent Endocytosis of Nanoparticles", Adv. Mater., 2009, 21, pp. 419-424.
Seydoux et al., "Size-dependent accumulation of particles in lysosomes modulates dendritic cell function through impaired antigen degradation", International Journal of Nanomedicine, 2014, 9, pp. 3885-3902.
Oh et al., "Endocytosis and exocytosis of nanoparticles in mammalian cells", International Journal of Nanomedicine, 2014, 9 (Suppl I), pp. 51-63.
Klionsky et al., "Guidelines for the use and interpretation of assays for monitoring autophagy", Autophagy, 2016, 12(1): 1-222.
Lin et al., "Pharmacological Promotion of Autophagy Alleviates Steatosis and Injury in Alcoholic and Non-alcoholic Fatty Liver Conditions in Mice", J. Hepatol., May 2013, 58(5): 993-999.
Perry et al., "The role of hepatic lipids in hepatic insulin resistance and type 2 diabetes", Nature, Jun. 5, 2014, 510(7503): 84-91.
Ozcan et al., "Calcium signaling through CaMKII regulates hepatic glucose production in fasting and obesity" Cell Metab., May 2, 2012, 15(5): 739-751.

(56) References Cited

OTHER PUBLICATIONS

Herzig et al., "CREB regulates hepatic gluconeogenesis through the coactivator PGC-1", Nature, 413, pp. 179-183, Sep. 13, 2001.
Barth et al., "Autophagy: assays and artifacts", J. Pathol., Jun. 2010, 221(2): 117-124.
Las et al., "The role of autophagy in β-cell lipotoxicity and type 2 diabetes", Diabetes, Obesity and Metabolism, 12 (Suppl. 2): 15-19, 2010.
Koga et al., "Altered lipid content inhibits autophagic vesicular fusion", FASEB J., Aug. 2010, 24(8): 3052-3065.
Lee et al., "Presenilin 1 maintains lysosomal $Ca^{2+}$ homeostasis by regulating vATPase-mediated lysosome acidification", Cell Rep., Sep. 1, 2015, 12(9): 1430-1444.
Colby et al., "Microscopy and Tunable Resistive Pulse Sensing Characterization of the Swelling of pH-Responsive, Polymeric Expansile Nanoparticles", Nanoscale, Apr. 21, 2013, 5(8): 3496-3504.
International Search Report and Written Opinion, dated Apr. 4, 2019, from corresponding International Application No. PCT/US2019/14410.

| Polymer name | Yield (%) | X:Y | X:Y (NMR) | $\overline{M}_n$ | $\overline{M}_w$ | Đ |
|---|---|---|---|---|---|---|
| PBSU | 95 | 0:100 | 0:100 | 11945 | 15289 | 1.28 |
| 25% PBFSU | 87 | 25:75 | 25:75 | 9077 | 13615 | 1.50 |
| 50% PBFSU | 93 | 50:50 | 52:48 | 14502 | 22478 | 1.55 |
| 75% PBFSU | 84 | 75:25 | 77:23 | 11587 | 18075 | 1.56 |
| 100% PBFSU | 94 | 100:0 | 100:0 | 14154 | 18117 | 1.28 |

Fig. 3A
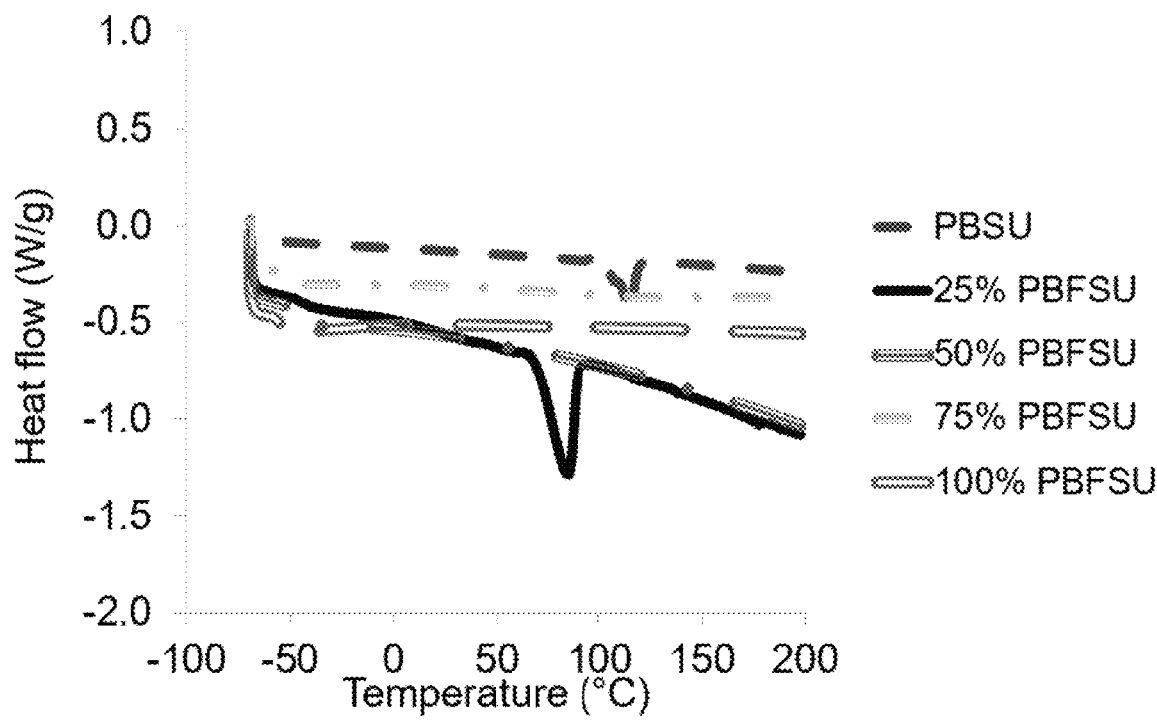
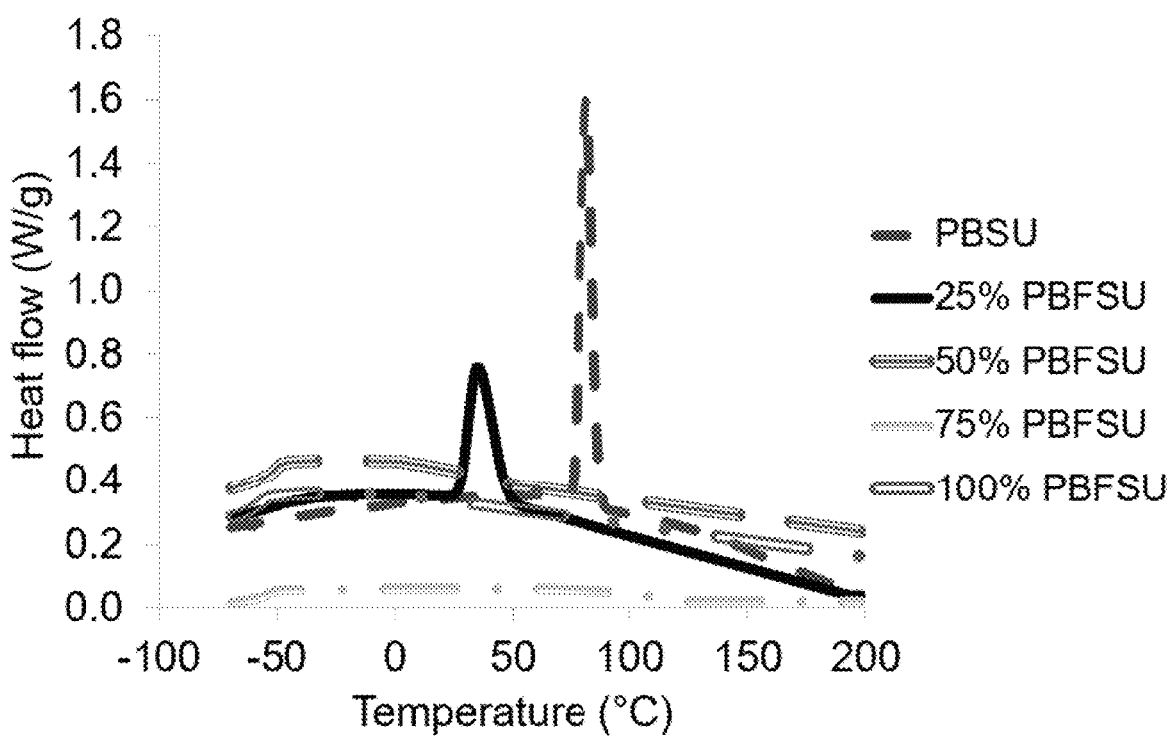
Fig. 3B

Fig. 10A
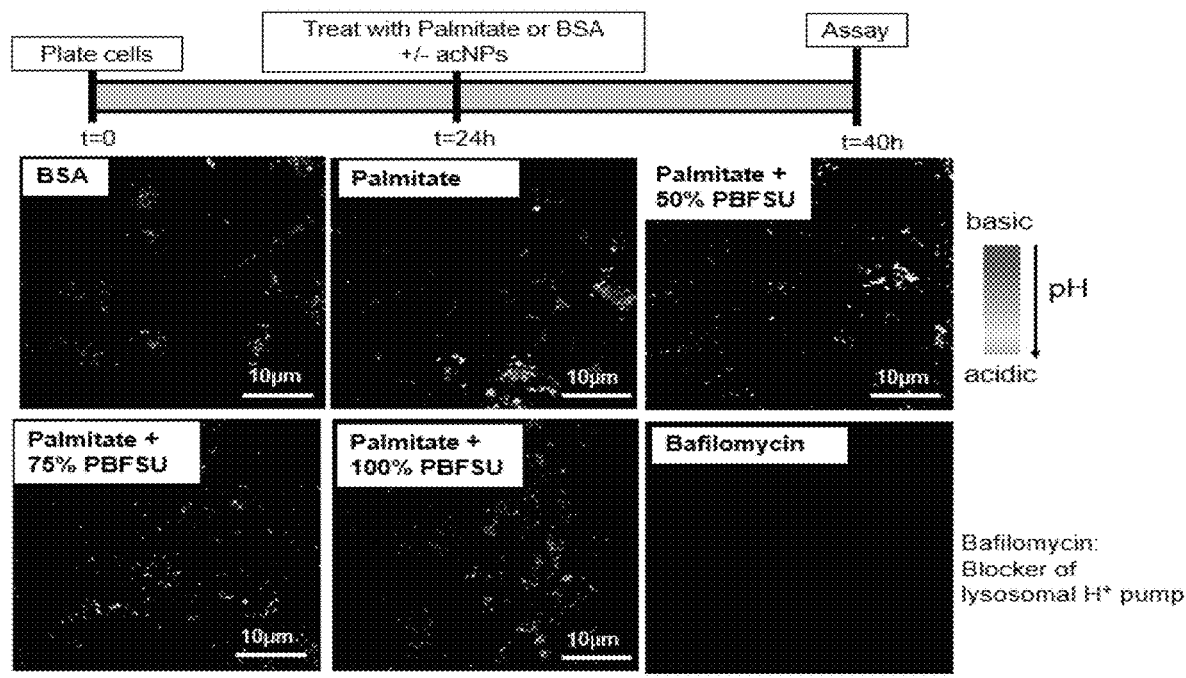
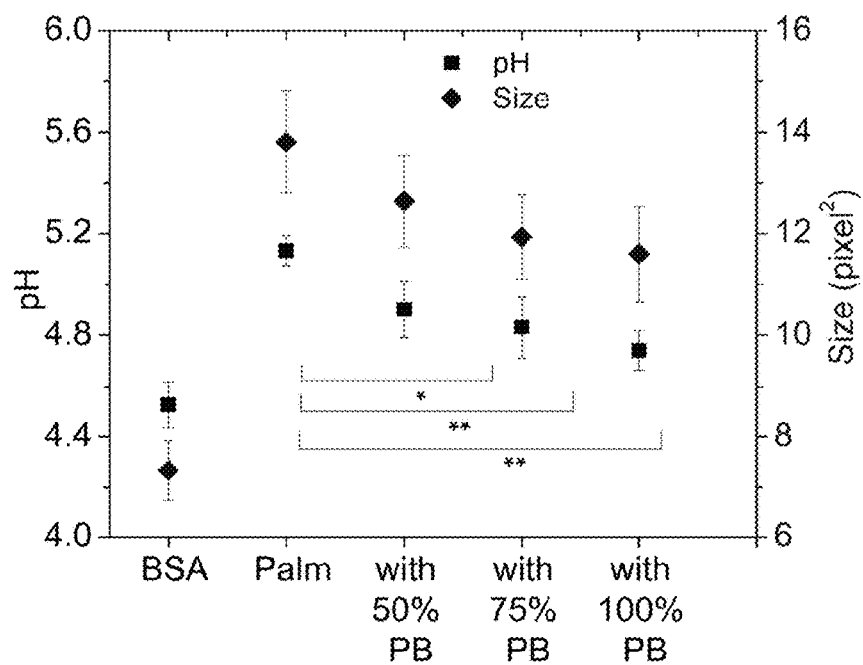
Fig. 10B

| Inhibitor | Pathway |
|---|---|
| NaN₃/2-deoxyglucose | General endocytosis |
| Chloropromazine | Clathrin-mediated |
| Hexamethylene amiloride | Macropinocytosis |
| Wortmannin | |
| Genistein | Caveolae-mediated |
| Methyl-β-cyclodextrin | Cholesterol dependence |

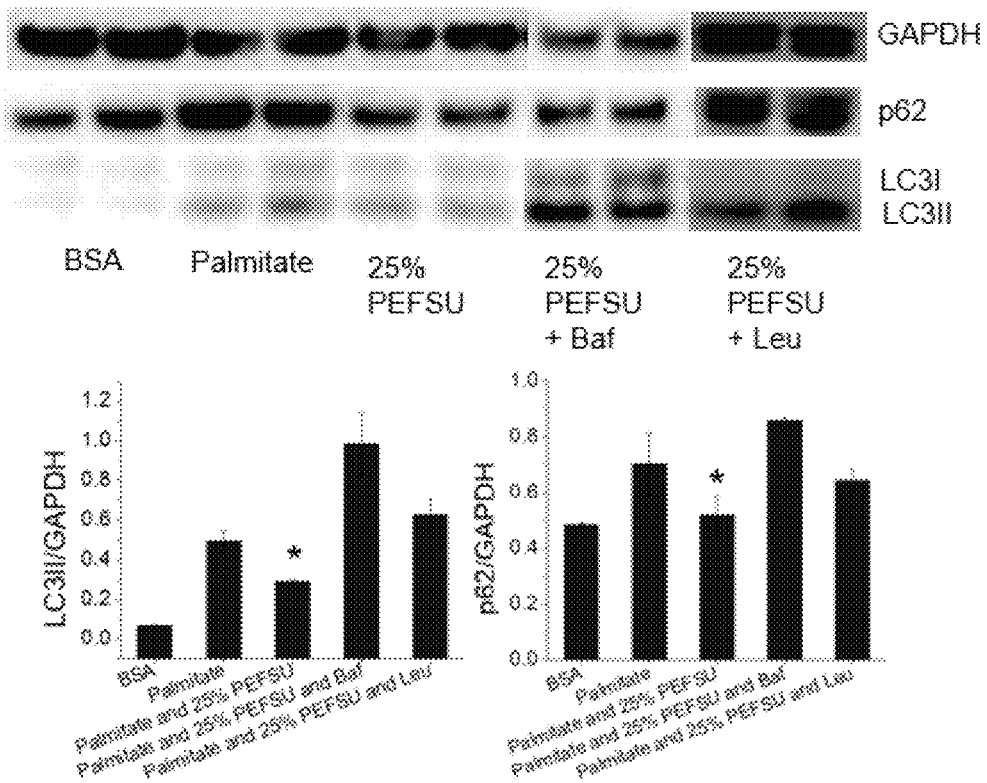
Fig. 21A
Fig. 21B
Fig. 21C
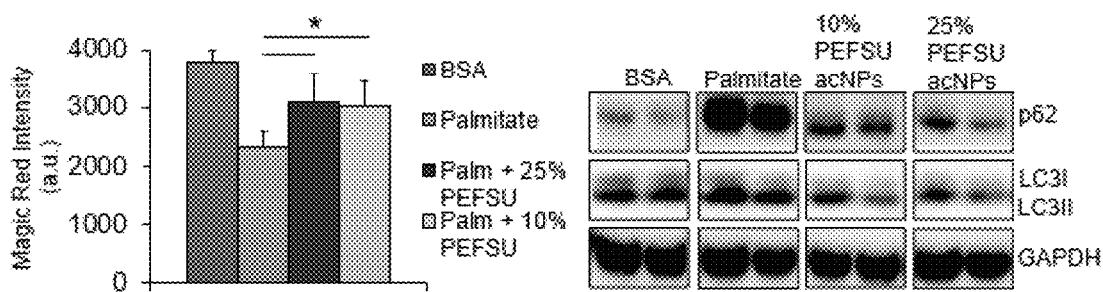
Fig. 22A
Fig. 22B

Fig. 23B                    Fig. 23C

ACIDIC NANOPARTICLES FOR RESTORATION OF AUTOPHAGY

CROSS-REFERENCE TO RELATED APPLICATIONS

This application claims the benefit of and priority to U.S. Patent Provisional Application No. 62/619,565, filed Jan. 19, 2018, the entire contents of which are incorporated herein by reference in its entirety.

BACKGROUND

Autophagy is an essential, evolutionarily conserved maintenance mechanism by which cells degrade long-lived proteins and organelles. This housekeeping process is especially critical in non-proliferating cells which rely on autophagy to remove damaged material that accumulates with aging. Fusion of the lysosome with the autophagosome also requires an acidic lysosome. Thus, lysosome acidity is an important local signal essential for lysosomal function and for maintaining autophagic flux. However, currently there are no tools available for manipulating lysosomal acidity both in vitro and in vivo. Current pharmacological and molecular tools can reduce lysosomal acidity; however, it is believed that no available tools exist to increase lysosomal. A number of disease states are associated with impaired lysosomal acidity, including but not limited to, type 2 diabetes, non-alcoholic fatty liver disease (NAFLD), and neurodegeneration.

Non-alcoholic fatty liver disease (NAFLD) is one of the most common liver diseases in the world today, affecting 20 to 30% of the general population. A variety of genetic and epigenetic factors contribute to the pathogenesis of NAFLD. Insulin resistance impairs the suppression of lipolysis in adipose tissue thereby increasing the levels of serum free fatty acids (FFA). FFAs are usually taken up by the liver and esterified into neutral triglycerides; however, an excess of saturated FFAs overwhelms the capacity of the liver to esterify FFA and induces lipotoxicity (LT). In hepatocytes under LT, disruption of autophagy concomitant with compromised lysosomal acidity has been reported. The disruption caused damaged organelles and proteins to accumulate in the cells and exacerbate declines in cellular functions and viability, promoting hepatocyte death and leading to progressive disease. NAFLD that is not treated becomes non-alcoholic steatohepatitis (NASH) that can progress to liver cirrhosis, which can seriously impair the liver's ability to function. A small percentage worsens into hepatocarcinoma, for which the only treatment option is a liver transplant with a reported low prospect of success.

No specific pharmacological agents have thus far been approved for the treatment of NAFLD. Current treatment options for NAFLD directed at prescribing insulin sensitizing agents include Thiazolidinedione (TZDs), Metformin, and injectable agents such as GLP-1 receptor agonist. These induce side-effects and the possible need for long-term therapy (Liu et al. *Proc. Natl. Acad. Sci. USA*, (2016) 113: 2288-2293). Another group of pharmacological agents that targets the autophagy pathway such as the mTOR pathway inhibitor Rapamycin has been used to treat autophagy related metabolic diseases, however, this agent can involve non-specific changes to important metabolic signaling pathways independent of autophagy induction. For this reason, it may be undesirable for long term usage. Lastly, preclinical compounds including GFT-505 (PPAR agonists) and OCA-LIVA® (Intercept Pharmaceuticals) are still in the process of clinical trials to fully characterize their efficiency.

SUMMARY

Non-alcoholic fatty liver disease (NAFLD) is the most common liver disease in the world today. Recently, it has been found that an increase in the level of liver free fatty acids (FFAs), termed as lipotoxicity (LT), causes an inhibition of autophagic flux with concurrent decrease in lysosomal acidity (i.e., the pH in the lysosome is increased), contributing to the pathogenesis of NAFLD. The problem to be solved is to provide a biocompatible method of restoring lysosomal acidity and autophagic flux. Accordingly, in the present invention we have synthesized novel biodegradable acid-activated acid releasing nanoparticles (acNPs) as a targeted strategy to manipulate lysosomal acidity and autophagy. These acNPs are based on fluorinated polyesters that are degraded at pH 6.0 (pH reported in dysfunctional lysosomes. Release of the acid(s) component from the nanoparticle further lower the lysosomal pH, thereby increasing autophagic flux and cellular function of hepatocytes under LT. The acNPs of the present invention is therefore useful as a therapeutic for treating NAFLD. Furthermore, the acNPs of the present invention are also useful for the treatment or prophylaxis of diseases associated with impaired lysosomal acidity. Such diseases include, but are not limited to, obesity, metabolic syndrome, type 2 diabetes (T2D), non-alcoholic fatty liver disease (NAFLD), liver transplantation, neurodegeneration (e.g., age-related dementia, Alzheimer's disease, Parkinson's disease, etc.).

In one aspect of the present invention, an acid-releasing fluorinated polyester nanoparticle is provided. The nanoparticle comprises a polyester and a tetrafluorosuccinic acid (TFSA) wherein the nanoparticle releases an acid when exposed to an environment having a pH of about pH 6.0. Because fluorinated polyesters exhibit low toxicity and high in vitro and in vivo biocompatibility, fluorinated polyesters nanoparticles are useful for medical applications, since they are readily taken up by the cells with minimal toxicity.

In one embodiment, the nanoparticle further comprises succinic acid (SA), The ratio of TFSA to SA ranges from 100:0 (TFSA:SA) to 10:90 (TFSA:SA) for example, the ratio of TFSA to SA comprises a ratio selected from the group consisting of about 10:90, about 15:85, about 20:80, about 25:75, about 30:70, about 35:65, about 40:60, about 45:55, about 50:50, about 55:45, about 60:40, about 65:35, about 70:30, about 75:25, about 80:20, about 15:15, about 90:10, about 95:5, and about 100:0.

In another embodiment, the nanoparticle comprises a polyester comprising a diol selected from the group consisting of ethylene glycol, propylene glycol, butylene glycol. For example, the acid-releasing fluorinated polyester nanoparticle may comprise the polyester, ethylene glycol, and TFSA (PEFSU); the polyester, propylene glycol and TFSA (PPFSU) or the polyester, butylene glycol and TFSA (PBFSU).

It is contemplated that the nanoparticle in the present invention is selected from the group consisting of 10% PEFSU; 15% PEFSU, 20% PEFSU, 25% PEFSU, 30% PEFSU, 35% PEFSU, 40% PEFSU, 45% PEFSU; 50% PEFSU; 55% PEFSU, 60% PEFSU, 65% PEFSU, 70% PEFSU, 75% PEFSU, 80% PEFSU, 85% PEFSU, 90% PEFSU, 95% PEFSU, 100% PEFSU, 10% PPFSU; 15% PPFSU, 20% PPFSU, 25% PPFSU, 30% PPFSU, 35% PPFSU, 40% PPFSU, 45% PPFSU; 50% PPFSU; 55% PPFSU, 60% PPFSU, 65% PPFSU, 70% PPFSU, 75%

PPFSU, 80% PPFSU, 85% PPFSU, 90% PPFSU, 95% PPFSU, 100% PPFSU, 10% PBFSU; 15% PBFSU, 20% PBFSU, 25% PBFSU, 30% PBFSU, 35% PBFSU, 40% PBFSU, 45% PBFSU; 50% PBFSU; 55% PBFSU, 60% PBFSU, 65% PBFSU, 70% PBFSU, 75% PBFSU, 80% PBFSU, 85% PBFSU, 90% PBFSU, 95% PBFSU, and 100% PBFSU.

In one embodiment, the nanoparticle is selected from the group consisting of 10% PEFSU, 15% PEFSU, 20% PEFSU, 25% PEFSU.

In a further embodiment, the nanoparticle is selected from the group consisting of 25% PPFSU, 50% PPFSU, 75% PPFSU, 100% PPFSU, 12. In yet another embodiment, the nanoparticle is selected from the group consisting of 30% PBFSU, 50% PBFSU, 75% PBFSU, 100% PBFSU.

In another embodiment, the nanoparticle has an average diameter that ranges from about 25 nm, or from about 50 nm up to about 200 nm, or up to about 150 nm, or up to about 100 nm.

In another embodiment, the nanoparticle preferred average diameter is less than about 100 nm.

In another embodiment, the population of the nanoparticle has a polydispersion index (PDI) of about 0.2 or less, or about 0.14 or less.

In yet another embodiment the nanoparticle has a size and a zeta potential that results in uptake into lysosomes when the nanoparticle is in contact with a cell.

In another aspect of the invention, the nanoparticle is useful to restore autophagic flux in the cell and/or enhances lysosome-autophagosome fusion capacity in the cell when the nanoparticle is taken up by a cell with impaired lysosomal acidification.

In one embodiment, the nanoparticle is effective to induce a short- and/or a long-term recovery of lysosomal function in hepatocytes exposed to fatty acids, or in B-cells exposed to fatty acids.

In another embodiment, the nanoparticle of is effective to normalize hepatocyte lipid content.

In a further embodiment, nanoparticle is effective to enhance B cell capacity to secrete insulin in response to glucose.

In another aspect of the invention, a pharmaceutical formulation is provided. The formulation comprises a plurality of nanoparticles described above and a pharmaceutically acceptable carrier. The pharmaceutical formulation comprises a unit dosage formulation that is substantially sterile.

In an embodiment, the pharmaceutical formulation is designed for administration via a route selected from the group consisting of oral delivery, isophoretic delivery, transdermal delivery, parenteral delivery, aerosol administration, administration via inhalation, intravenous administration, and rectal administration.

Another aspect of the invention provides a method of promoting autophagy in cells of a mammal by contacting the cells with the plurality of nanoparticles described above. The method involves administering to the mammal an effective amount of nanoparticles and/or the pharmaceutical formulation above.

In one embodiment, the method treats a pathology in a mammal that responds favorably to restoration of lysosomal function by administering to the mammal an effective amount of the nanoparticles of the instant invention in a pharmaceutical formulation.

In another embodiment, the method provides treatment in a mammal having a disease state associated with impaired lysosomal acidity. The disease state is selected from the group consisting of obesity, metabolic syndrome, type 2 diabetes (T2D), non-alcoholic fatty liver disease (NAFLD), and neurodegenerative pathology.

In a further embodiment, the disease state comprising a neurodegenerative pathology is selected from the group consisting of age-related dementia, Parkinson's disease, and Alzheimer's disease.

In one embodiment, the method is effective for restoring autophagic flux under conditions that impair lysosomal acidification.

In another embodiment, the method is effective to enhance lysosome-autophagosome fusion capacity.

In another embodiment, the method is effective to enhance lysosomal hydrolase activity.

In another embodiment, the method produces short-term or long-term recovery of lysosomal function. For example, the method is effective to produce short-term or long-term recovery of lysosomal function in hepatocytes exposed to fatty acids and normalizes lipid content in the hepatocytes.

In another further embodiment, the method is effective to produce short-term or long-term recovery of lysosomal function in B-cells exposed to fatty acids and to enhance B-cell capacity to secrete insulin in response to glucose.

In yet another embodiment, the method provides treatment in a mammal that is a human a non-human mammal by administering an effective amount of acNPs. The acNPs can be administered intravenously or by other modes known in the art.

While in certain of the foregoing embodiments, it will be recognized that the TFSA can be substituted with other acids, in particular other acids having a pKa of less than about 2, or with a pKa of ~1.6 or less for the nanoparticle of the present invention.

BRIEF DESCRIPTION OF THE DRAWINGS

FIGS. 3A and 3B: Thermal behavior of PBFSU polyesters by differential calorimetric scanning (DSC) at the rate of: 10° C./min, heating curve (FIG. 3A) and 5° C./min, cooling curve (FIG. 3B).

FIG. 10A shows confocal images of HepG2 cells treated with BSA (control), Palmitate or Palmitate+PBFSU acNPs. FIG. 10B shows the quantification of the lysosomal pH and size measured using MetaMorph® analysis software (panel B), n=3, *p<0.05.

FIG. 12A: $^1$H NMR, FIG. 12B: $^{13}$C NMR and FIG. 12C: $^{19}$F NMR spectra.

FIG. 13A: Scanning electron micrographs of various acNPs (scale bar=200 nm). FIG. 13B: pH changes over time of acNPs with different polymer compositions in pH 6.0 and pH 7.4 buffer. Note pH did not change significantly when 25% PEFSU was added to the pH 7.4 buffer compared to the pH 6.0 buffer, showing activation of acidification only at pH 6.0.

FIG. 16A shows super-resolution images of HepG2 cells treated with rhodamine-labeled acNPs (red) and stained with the lysosome dye, LysoTracker™. FIG. 16B is a list of inhibitors useful for identifying acNPs uptake into cells and the target pathways for the acNPs.

FIG. 17A: Effects of various acNP concentration on the viability of cells incubated with PESU or 25% PEFSU. Cells were incubated with a range of acNP concentrations for 24 hrs. Concentrations of acNPs up to 1000 μg/ml did not induce significant cell death. Based on this study, a treatment dose of 100 μg/ml was chosen for further studies. FIG. 17B: Quantification of rhodamine-labeled acNP (Rho-acNP) uptake in HepG2 cells by flow cytometry. Rho-acNP uptake occurs within 4 hours, with complete uptake after 24 hours of incubation. (Data=mean±SD, n=3, *=p<0.05). FIG. 17C: Confocal microscopy images showing the uptake of Rho-acNPs in HepG2 cells (right panel) and is colocalized in the lysosomal compartment (left panel) that is stained with LysoSensor™; blue channel (middle panel). Bar, 10 μm.

FIG. 18A: LysoSensor™ images of INS1 cells chronically treated with complexed palmitate:BSA (4:1 ratio) with or without acNPs. FIG. 18B: Quantification of the changes in pH caused by palmitate:BSA and acNPs. FIG. 18C: acNPs prevent cell death. Treatment with palmitate:BSA induced 7 fold more cell deaths compared to BSA control. Addition of a 25% PEFSU acNPs reduced the cell death significantly compared to BSA control. (Data=mean±SD, n=3, *=P<0.05)

FIG. 19A: Schematic of experimental protocol for cells incubated with BSA (control) or Palmitate in the absence (control) or presence of 25% PEFSU acNPs, followed by assay for lysosomal acidity, autophagy, or cellular function. FIG. 19B: Confocal microscopy images of HepG2 cells incubated with BSA (top, left panel), Palmitate (top right panel), Palmitate and 25% PEFSU (bottom right panel) and Bafilomycin (Baf), an inhibitor of lysosomal acidification (bottom left panel). Cells were stained with pH-sensitive LysoSensor™ dye to assess lysosome acidity. 100 μM Baf was used to demonstrate specificity of LysoSensor™ staining of lysosomes. Bar, 10 μm. FIG. 19C: Mean lysosomal pH (□) and lysosomal area (◇) per cell following treatment of cells with BSA (control), Palmitate (control) and Palmitate and 25% PEFSU. The results showed significant restoration of lysosomal pH in cells treated with Palmitate and 25% PEFSU compared with cells treated with Palmitate only, n=3 experiments for pH values and for size values with 20-30 cells analyzed per experiment. FIG. 19D: Assessment of lysosomal cathepsin L activity by Magic red cathepsin L fluorescent substrate assay in HepG2 cells treated with BSA (control), Palmitate (control) and Palmitate and 25% PEFSU. The results showed significant restoration of lysosomal enzyme activity with 25% PEFSU acNPs treatment (Data=mean±SD, n=3, *=p<0.05).

FIGS. 21A-21C illustrate the functional effects of acNPs on autophagic flux in HepG2 cells treated with BSA (control), Palmitate (control) and Palmitate 25% PEFSU. FIGS. 21A-21C: The protein levels of LC3-II, GAPDH and p62 were determined by Western blot densitometry analysis. Treatment with palmitate induced accumulation of LC3II and p62, while clearance of accumulated autophagosomes, LC3-II and p62 proteins, were observed upon treatment with 25% PEFSU acNPs. (Data=mean±SD, n=3, *=p<0.05).

FIGS. 22A and 22B illustrate functional changes in cathepsin L activity and autophagic flux induced by acNPs. FIG. 22A: HepG2 cells chronically incubated with palmitate reduce cathepsin L activity that is rescued by acNPs. FIG. 22B: HepG2 cells chronically incubated with palmitate increase p62 and LC3II accumulation that is partially reversed by acNPs. (Data=mean±SD, n=3, *=p<0.05)

FIGS. 23A-23C show the effect of acNPs on lipid droplets accumulation in HepG2 cells following treatment with BSA, palmitate and 25% PEFSU acNP. FIG. 23A: HepG2 cells stained with Nile Red dye for 15 minutes showed accumulation in the lipid vesicles. Fluorescence microscopy indicated significant reduction in lipid droplets density after 25% PEFSU acNPs treatment in HepG2 cells exposed to palmitate, n=30-50 cells per condition. FIG. 23B: Quantification of lipid droplets in HepG2 cells treated with BSA, palmitate or palmitate+25% PEFSU. FIG. 23C: Gluconeogenesis of HepG2 cells stimulated by 100 nM insulin.

DETAILED DESCRIPTION

Autophagy is an essential, evolutionarily conserved maintenance mechanism by which cells degrade long-lived proteins and organelles. This housekeeping process is especially critical in non-proliferating cells, which rely on autophagy to remove damaged material that accumulates with aging. The key steps of autophagy are autophagosome recruitment and engulfment of cellular contents, followed by autophagosome fusion with an acidic lysosome. Hydrolase enzymes in the lysosome are dependent on a sufficiently low pH to properly degrade the engulfed material. Fusion of the lysosome with the autophagosome also requires an acidic lysosome. Thus, lysosome acidity is an important local signal that is essential for lysosomal function and for maintaining autophagic flux.

The compositions and methods described herein stemmed, inter alia, from a lack of available tools for manipulating lysosomal acidity both in vitro and in vivo. Specifically, current pharmacological and molecular tools capable of reducing lysosomal acidity, i.e., increase pH (e.g., bafilomycin) are known. However, no tools exist to increase lysosomal acidity, i.e. reduce pH.

A number of disease states are associated with impaired lysosomal acidity including but not limited to: metabolic syndrome, type 2 diabetes, non-alcoholic fatty liver disease (NAFLD), neuro-degeneration and cardiomyopathy of the obese. The ability to directly determine disease progression has been severely hampered by the inability to appropriately manipulate lysosomal pH. For example, studies showed that pancreatic β-cells exposed chronically to elevated glucose and saturated fatty acids have reduced autophagic flux stemming from defective acidification of lysosomes. To determine the role of reduced lysosomal acidification in β-cell dysfunction, we have synthesized and characterized novel nanoparticles (NPs) that acidify defective lysosomes upon acute activation by ultraviolet light. Photo-activation of these nanoparticles provided a 2-hour restoration of lysosomal acidity. Subsequent analyses demonstrated that indeed restoration of lysosomal acidity in pancreatic β-cells exposed to glucolipotoxicity normalizes autophagic flux and glucose-stimulated insulin secretion.

However, because of the requirement for an external trigger (i.e., ultraviolet light) and the restoration of lysosomal acidity is short-lived (2 h), the use of photo-activatable nanoparticles (paNPs) is limited to short-term experiments and does not allow for assessment of the benefits of long-term and in vivo restoration of lysosomal acidity in a human or non-human animal with dysfunctional lysosomes. Accordingly, we developed and characterized a new generation of nanoparticle that is activated by an internal lysosomal trigger. These new generation of nanoparticles (acid-activated acid-releasing nanoparticle or acNPs) can be activated even by impaired lysosomes that still retain a mildly acidic environment (~pH 6).

Figure 1:
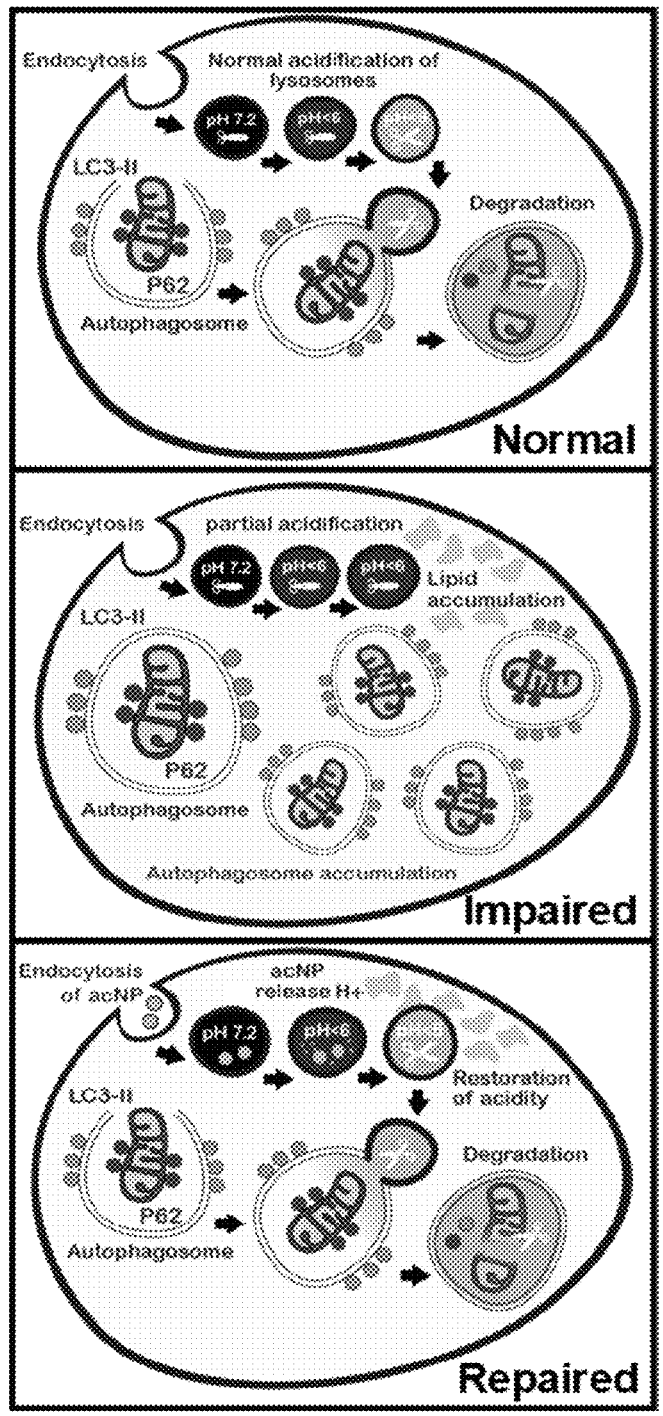
FIG. 1 illustrates the use of acNPs of the present invention for the treatment of obesity, Type II diabetes, and non-alcoholic fatty liver disease (NAFLD). Obesity, type II diabetes, and NAFLD are associated with impaired lysosomal acidification leading to the arrest of autophagic flux and accumulation of autophagosomes. The acNPs described herein target the lysosome. In impaired cells, lysosomal pH is partially acidified, and hence does not fuse with autophagosomes. Autophagic flux is inhibited, and autophagosomes that encapsulate lipids are accumulated in the cells, reducing the clearance of lipids. After entry into the lysosome, the acNPs will release acids to restore the acidity of the lysosome, thereby restoring the fusion with autophagosomes, lysosomal hydrolase activity and autophagic flux.
Figures 2A, 2B:
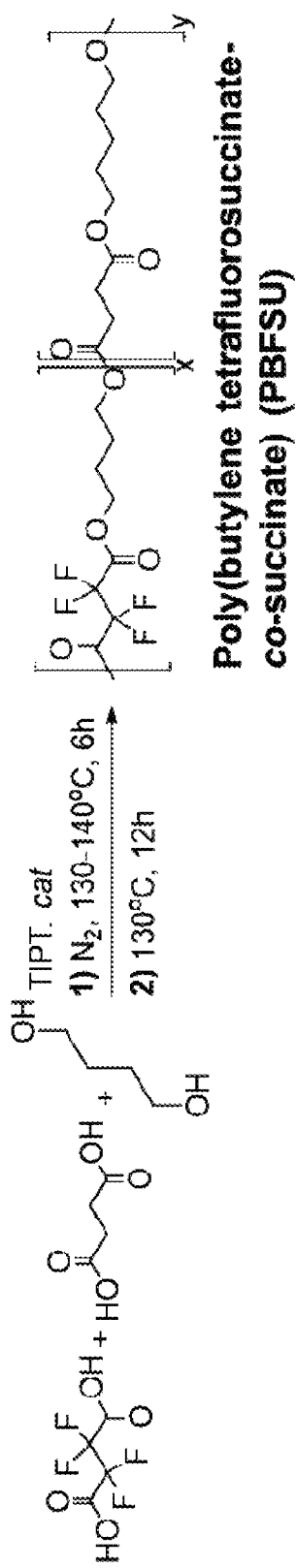
FIG. 2A shows a schematic diagram for the synthesis of PBFSU.
FIG. 2B: Summary of the chemical and physical properties of PBFSU polymers.
Figure 2C:
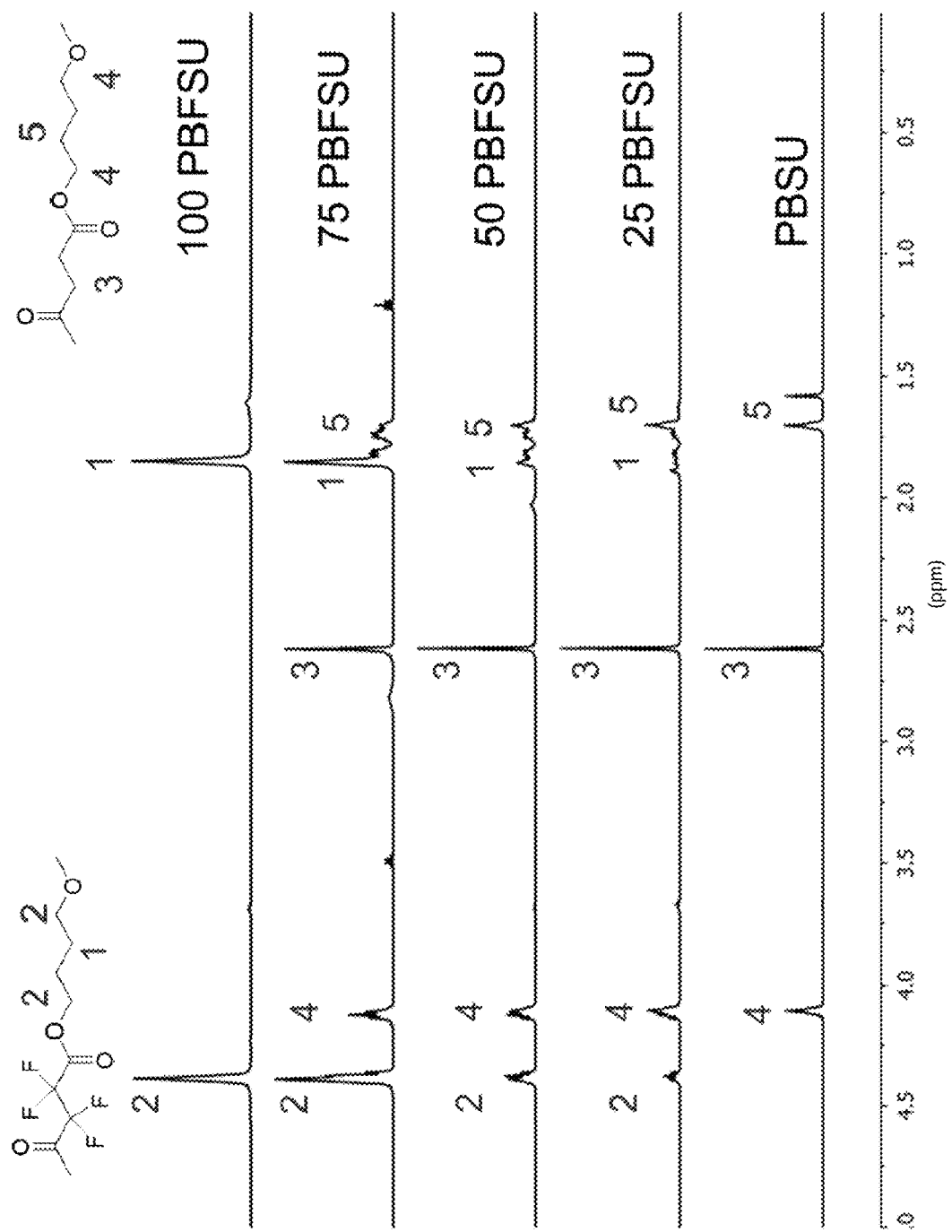
FIGS. 2C-2E: NMR spectra of PBFSU polymers: $^1$H (FIG. 2C), $^{13}$C (FIG. 2D), and $^{19}$F (FIG. 2E).
Figure 2D:
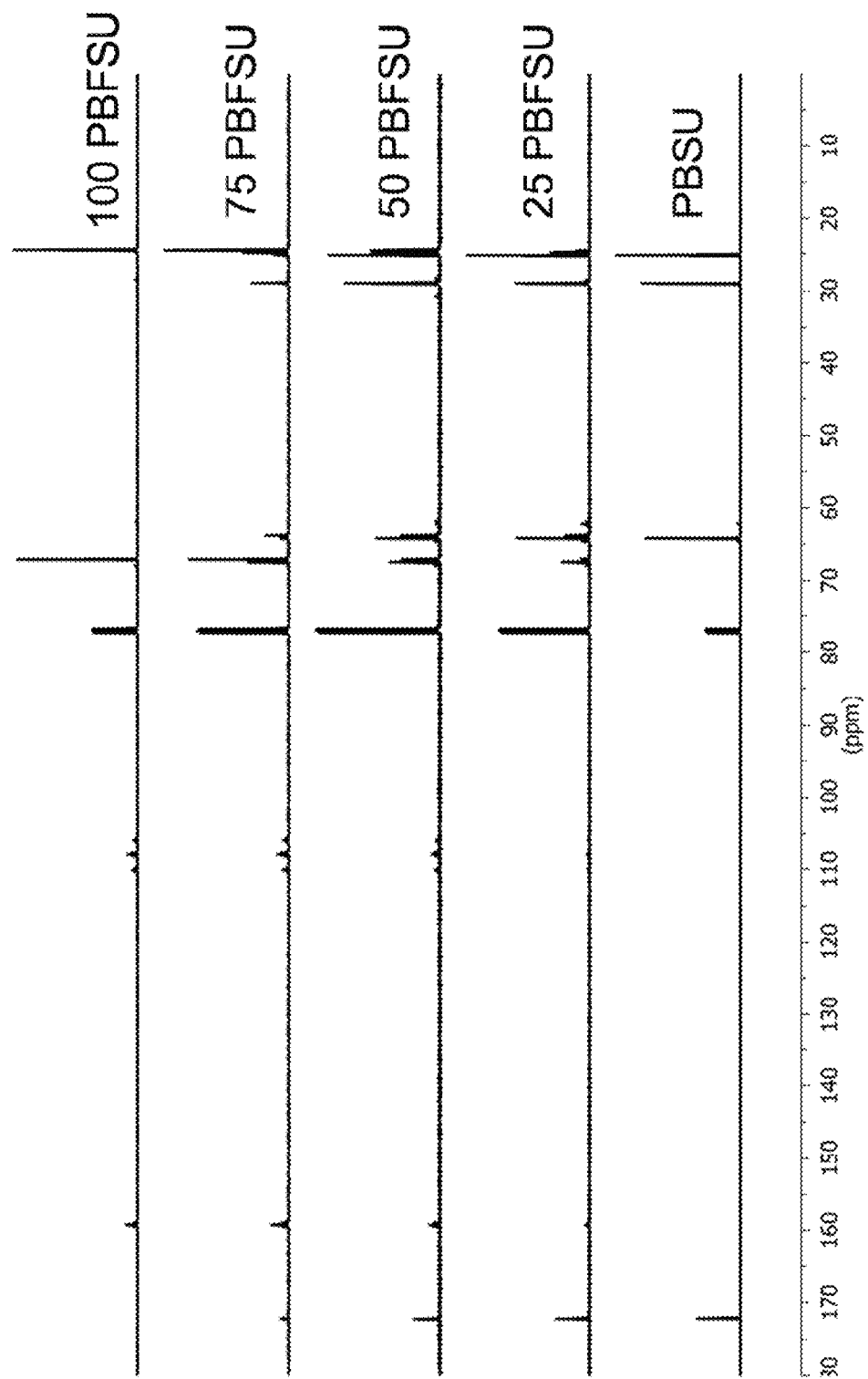
Figure 2E:
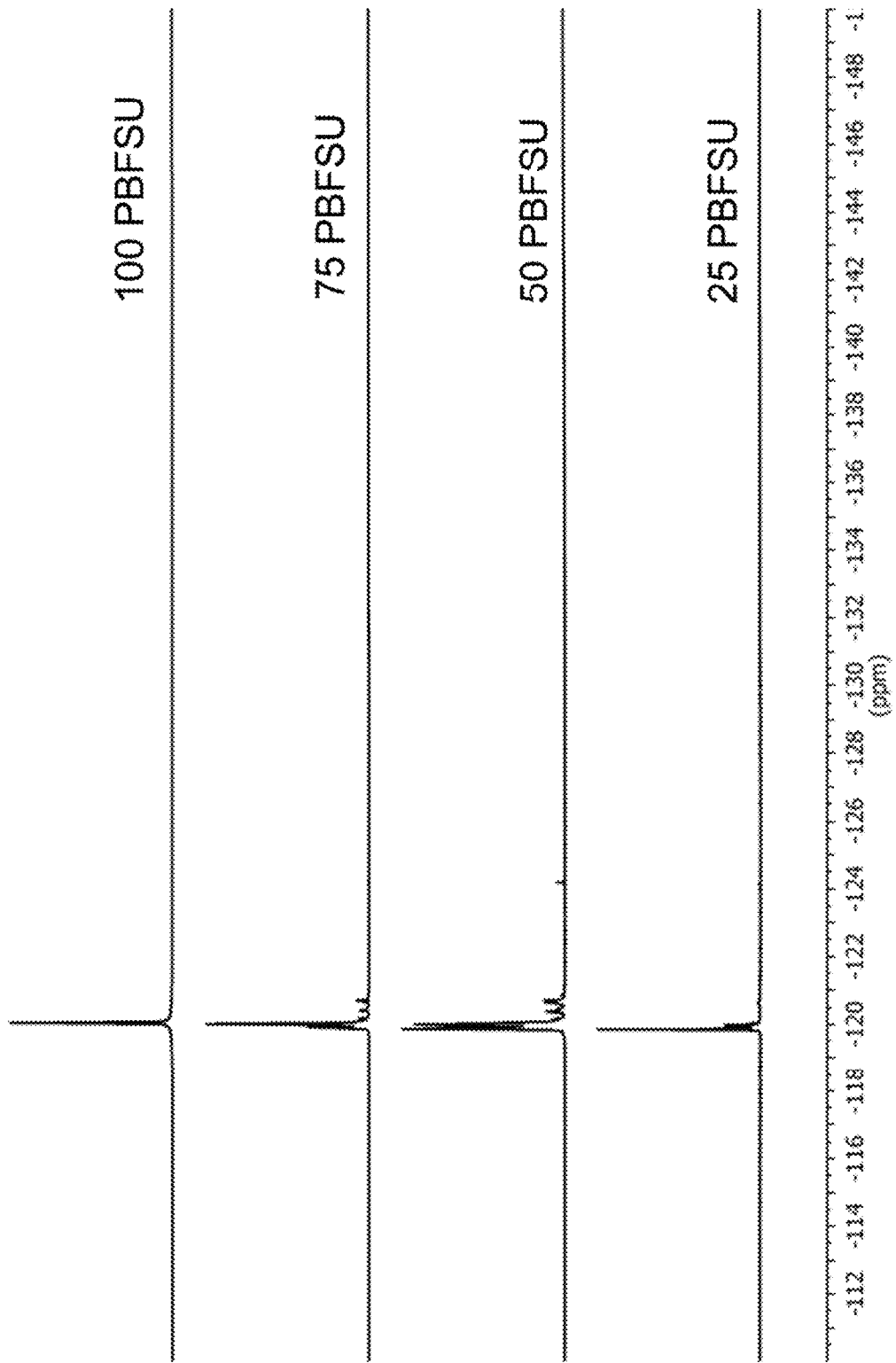

These acid-activated acid-releasing nanoparticles (acNPs) can be used to restore autophagic flux and cellular function in cellular models of non-alcoholic fatty liver disease and β-cell dysfunction. FIG. 1 provides a model detailing the ability of acNPs to restore autophagic flux in cells exposed to a high lipid environment.

Without being bound to a particular theory, these nanoparticles can be utilized in vivo via an intravenous administration or other modes of administration known in the art. These nanoparticles have the potential to be a significant development for studying diseases with impaired lysosomal acidity, including their use for restoring lysosomal acidification to treat these diseases. In addition, drug developers can use the acNPs to validate drug targets in the lysosome acidification pathways for the disease of interest.

Because long-term restoration of lysosomal acidification has not been possible previously, the acNPs described herein are the first:

1) Tool to restore lysosomal acidification for an extended, continuous period to facilitate mechanistic studies;

2) Tool to enable researchers to interrogate the benefit of targeting impaired lysosomal acidification, and therefore empower drug developers to validate lysosomal acidification as a therapeutic target;

3) NP that will sense its entry to the targeting organelle and that is self-activated inside the organelle;

4) Targeted intervention by which lysosomes can be acidified without interfering with other organelles pH;

5) Lysosome acidifying intervention suitable for utilization in vivo, given the precedent of NP use in vivo.

It is noted that non-alcoholic fatty liver disease (NAFLD) is the most common liver disease in the world today. Recently, it has been found that an increase in the level of liver free fatty acids (FFAs), termed as lipotoxicity (LT), causes an inhibition of autophagic flux with concurrent decrease in lysosomal acidity, contributing to the pathogenesis of NAFLD. In one aspect of the present invention, a novel biodegradable acid-activated acid releasing nanoparticles (acNPs) is synthesized to strategically target and manipulate lysosomal acidity and autophagy. In one aspect of the invention, the acNPs are based on fluorinated polyesters that can be degraded at pH 6.0 (which is the pH reported in dysfunctional lysosomes), to release component acids—TFSA (tetrafluorosuccinic acid) and SA (succinic acid) that further lower the lysosomal pH, thereby increasing autophagic flux and cellular function of hepatocytes under LT. The acNPs described herein can serve as a potential therapeutic in restoring NAFLD and other dysfunctional lysosomal diseases.

The acNPs of the present invention can be used to promote autophagy in a number of contexts, including the treatment of cardiomyopathy, age-related dementia, Alzheimer's disease, Parkinson's disease, and lysosomal storage disorders as well as for the treatment of pathologies in a mammal that responds favorably to restoration of lysosomal function. In one aspect of the invention, the acNPs can be used in the treatment or as a prophylaxis of a disease associated with impaired lysosomal acidity. Such diseases include, but are not limited to obesity, hyperlipidemia, hypertension, metabolic syndrome, type II diabetes (T2D), liver diseases such as non-alcoholic fatty liver disease (NAFLD), non-alcoholic steatohepatitis (NASH), liver cirrhosis or liver cancer, neurodegeneration (e.g., age-related dementia, Alzheimer's disease, Parkinson's disease, etc.). In another embodiment, the acNPs can be administered to a liver to be transplanted into a subject in need of transplantation. In another embodiment, the liver for transplantation is de-lipidized by perfusing the liver with acNPs of the present invention.

Without being bound by a particular theory, it is believed the nanoparticles (acNPs) described herein and illustrated in the Examples, enable localized restoration of lysosomal pH, autophagic flux, and cellular function in cellular systems where excess lipid inhibits autophagy. These observations have been extended to in vivo models. These novel acNPs deliver acid into the compromised lysosomal compartment via an internal lysosomal trigger to restore autophagic flux and cellular function. It is believed that the acNPs of the present invention are the first available pharmacological or molecular tool capable of adjusting lysosomal pH to the acidic condition required for the lysosome to function normally.

Decreased lysosomal acidity (pH>6) inhibits autophagic flux in hepatocytes and β-cells exposed to high levels of fatty acids (FAs). In one aspect, acNPs prepared from fluorinated polyesters are taken up and constitutively activated in dysfunctional lysosomes at pH 6. Different compositions of polymers were formulated and used to determine the formulations that have the proper acidification rate, lysosome targeting, and restoration of lysosome acidity under conditions that inhibit lysosomal acidification.

In certain embodiments, the acNPs are prepared from polyesters that degrade into their acid and alcohol constituents upon exposure to a mildly acidic environment. To ensure that the acid is released only into dysfunctional lysosomes and that further acidification occurs, in certain embodiments, fluorinated polyesters containing tetrafluorosuccinic acid (TFSA) are used. Fluorinated polyesters are extensively used in medical applications, where they exhibit low toxicity and high in vitro and in vivo biocompatibility. In general, polyesters do not readily hydrolyze in aqueous environment at pH 7-7.4. However, in the presence of a slightly acidic environment (pH 6.0), they undergo hydrolysis, degrade, and release acid. The challenge, therefore, was in the further lowering of the surrounding pH upon hydrolysis and NP degradation. Previously synthesized biodegradable polyesters composed of acids such as glycolic acid or succinic acid (SA), which have relatively high pKa values (e.g., glycolic acid=3.83, succinic acid=5.6 and 4.2), lowered the pH only slightly and therefore is insufficient to restore the pH in the lysosomes. However, in the polyester nanoparticles illustrated herein, we used TFSA, which possesses a lower pKa of ~1.6. Thus, acNPs enable more significant restoration of lysosomal pH via the release of a stronger acid.

We hypothesized that acNP compositions of polyesters possessing: 1) a greater amount of TFSA to SA will give a greater acidic response in buffer and lysosomal compartments; and 2) greater hydrophobicity (by increasing the number of methylene carbons present in the diol, e.g., ethylene to propylene to butylene glycol, within the polyester) will degrade more slowly and deliver acid over a longer time period. Accordingly, in one embodiment, the TFSA to SA content is varied in the synthesis of the acNPs. In another embodiment, the length of the glycol chain is varied. A shorter glycol chain results in greater acidification, and a longer glycol chain results slower degradation of the acNPs, allowing delivery of the acid over a longer time. To modulate the degree of acidification, we synthesized a series of polyesters and corresponding acNPs based on different ratios of TFSA:SA, and different types of diols—ethylene glycol, propylene glycol or butylene glycol that activate at pH~6 to further acidify the lysosomal lumen to normal levels (pH~4.5). It is recognized that the ethylene glycol, propylene glycol, and butylene-glycol diols are illustrative and non-limiting. Other linear hydrocarbon-based diols, for example, hexanediol, polyethylene glycol, can also be used to generate acNPs. In another embodiment, branched diols are used to generate acNPs of the present invention. Examples of branched diols, include but are not limited to, glycerol and poly(ethylene glycol) star polymers. Using the teaching provided herein, other suitable diols are recognized by one of skill in the art.

In a further embodiment, the acNPs comprises a polyester wherein the chain length of the diol and the ratio of tetrafluorosuccinic acid to succinic acid are varied. By varying the polymer compositions and/or the ratio of tetrafluorosuccinic acid to succinic acid in the acNPs, the rate and degree of acidification can be modulated. Higher TFSA content result in increased rate of lysosomal acidification.

Furthermore by varying the polymer compositions and/or the ratio of tetrafluorosuccinic acid to succinic acid in the acNPs, the acNPs can be administered to human or non-human mammals in need of treatment for a short duration or long term. In addition. varying the polymer compositions and/or the ratio of tetrafluorosuccinic acid to succinic acid provides stability, and hence storage, with or without the need to control the temperature in which the acNPs are stored.

In one illustrative, but non-limiting embodiment, the polymers were synthesized via a polycondensation method according to Scheme I below:

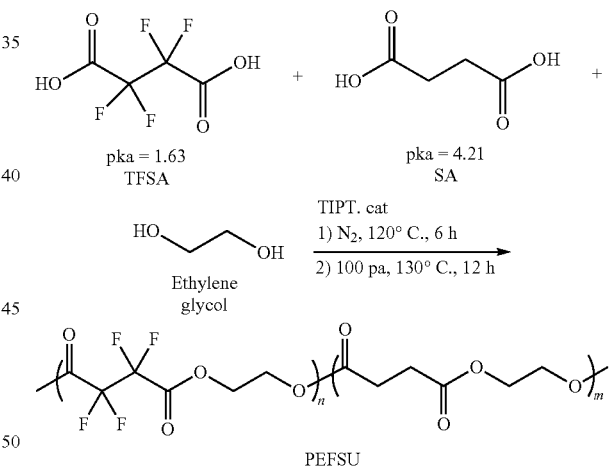

In various embodiments, the monomer ratios, and glycol types are varied to vary the resulting polymer. The final composition and molecular weights are characterized and verified via, e.g., $^1$H, $^{13}$C NMR and gel permeation chromatography techniques. The results are shown in the Examples 1 and 2. We synthesized a library of polymers that vary in both TFSA:SA ratio and either ethylene glycol, propylene glycol or butylene glycol (see Table 1). Characterization chemical composition and molecular weights number average molecular weight, Mn, weight average molecular weight, Mw, and polydispersity, D. of, inter alia polyesters 1 (10% PEFSU), 4 (25% PEFSU), 5 (PESU) and 12 (50% PBFSU) are shown in Table 1 (see, also, characterization of these polymers in the Examples 1 and 2).

TABLE 1

Illustrative, but non-limiting library of acNPs.

| No | Polymer name | TFSA:SA | TFSA:SA (NMR) | Glycol | $\overline{M_n}$ (g/mol) | $\overline{M_w}$ (g/mol) | Đ |
|---|---|---|---|---|---|---|---|
| 1 | 10% PEFSU | 10:90 | 10:90 | Ethylene | 5764 | 7205 | 1.25 |
| 2 | 15% PEFSU | 15:85 | 14:86 | Ethylene | 6881 | 7293 | 1.06 |
| 3 | 20% PEFSU | 20:80 | 21:79 | Ethylene | 6862 | 7891 | 1.15 |
| 4 | 25% PEFSU | 25:75 | 24:76 | Ethylene | 6993 | 8531 | 1.22 |
| 5 | PESU | 0:100 | 0:100 | Ethylene | 5125 | 6611 | 1.29 |
| 6 | 25% PPFSU | 25:75 | 27:73 | Propylene | 16526 | 23896 | 1.47 |
| 7 | 50% PPFSU | 50:50 | 53:47 | Propylene | 10489 | 13425 | 1.28 |
| 8 | 75% PPFSU | 75:25 | 72:27 | Propylene | 15740 | 23610 | 1.50 |
| 9 | 100% PPFSU | 100:0 | 100:0 | Propylene | 12402 | 15750 | 1.27 |
| 10 | PPSU | 0:100 | 0:100 | Propylene | 11479 | 15956 | 1.39 |
| 11 | 25% PBFSU | 25:75 | 25:75 | Butylene | 9077 | 13615 | 1.50 |
| 12 | 50% PBFSU | 50:50 | 52:48 | Butylene | 14502 | 22478 | 1.55 |
| 13 | 75% PBFSU | 75:25 | 77:23 | Butylene | 11587 | 18075 | 1.56 |
| 14 | 100% PBFSU | 100:0 | 100:0 | Butylene | 14154 | 18117 | 1.28 |
| 15 | PBSU | 0:100 | 0:100 | Butylene | 11945 | 15289 | 1.28 |

In certain illustrative, but non-limiting embodiments, this diameter is selected because 50-100 nm NPs are readily taken into the lysosome via the endocytic pathway (20, 21). Illustrative results of acNPs formed from polyesters 1 (10% PEFSU), 4 (25% PEFSU), 5 (PESU) and 12 (50% PBFSU) demonstrate relatively small size and uniform distribution (diameter<100 nm, PDI<0.14) according to dynamic light scattering and scanning electron microscopy studies.

In certain embodiments, acNPs that alter plasma pH in vivo when between pH 5 to pH 6.0. The acNPs is capable of significantly decreasing the pH from 6 to 3.

Rate of acNPs Cellular Uptake and Localization to the Endosomal/Lysosomal Compartment.

Characterization of the Rate of Uptake of acNPs into Cells and Lysosomes.

The invention provides a library of polyesters and acNPs. In certain embodiments, polymer synthesis yields are >60%, with dispersity (Mw/Mn)<1.4, and MW within 10% of expected MW. In some embodiment, the diameter of the acNPs is about 75 mm with a PDI<0.1. In a further embodiment, the diameter of the acNPs is about 100-120 nm with a PDI of 0.1-0.2. In another embodiment, the diameter of the acNPs is about 50-100 nm. The acNPs of the present invention can be generated by using the mini-emulsion technique or by using a LV-1 Microfluidizer (Microfluidics Corp). The acNP composition-acidification, i.e., the relationship between TFSA content to glycol chain length is determined to optimize polymer composition and lysosomal acidification. The acNPs of the present invention are not cytotoxic to the cells and may be taken up by the cells via micropinocytosis, endocytotosis (clathrin or caveolin-mediated), phagocytosis, or micropinocytosis. After entry into the cells, the acNPs are localized to the lysosome where the acNPs acidify the lysosomes to its normal pH of about 4 to about 4.5 within four hours A potential limitation in the synthesis of NPs is the instability of acNPs for long-term storage (>30 days) because of aggregation. In one embodiment, the NPs are lyophilized following synthesis. In another embodiment, one or more cryo-protectants (e.g., trehalose, mannose or sucrose) are added. The cryo-protectants serve to stabilize the NP suspension and to increase its ease of re-suspension for further usage. The acNPs of the present invention enable long-term restoration of autophagic flux under conditions that impair lysosomal acidification.

In one aspect of the invention, the acNPs provide short- and long-term restoration of lysosomal function and autophagic flux in diseased cells with impaired lysosomal acidification. In one embodiment, the acNPs provides short- and long-term recovery of lysosomal function and autophagic flux in hepatocytes and β-cells exposed to excess FAs. In one embodiment, the acNPs enhance lysosome-autophagosome fusion capacity, lysosomal hydrolase activity, and autophagic flux in cells that are chronically exposed to FA. The acNPs enable continuous and long-term restoration of optimal lysosomal pH. Validation experiments showed that acNPs can provide short- and long-term restoration of lysosomal function and autophagic flux (acNPs can decrease lysosomal pH in B cells after 4 hours of incubation) in vitro disease models of β-cell dysfunction.

The inhibition of autophagic flux caused by chronic exposure to FAs is a result of reduced lysosomal acidity, which compromises lysosome fusion with autophagosomes and the degradation of the autophagosome content. In one embodiment, the acNPs enhance lysosome-autophagosome fusion capacity, lysosomal hydrolase activity, and autophagic flux in cells that are chronically exposed to FA.

In another embodiment, the acNP restores hydrolase activity in the lysosomes. Lysosomal enzyme activities in the cells include cathepsin (i.e., Cathepsin A, B, C, D, E, K, L, O, S, V), glucocerebrosidase (GBA), or LAMP (i.e. LAMP1, LAMP 2, LAMP 5.

In another embodiment, the acNP restores autophagic flux in cells with lysosomal dysfunction. The cells with lysosomal dysfunction may include cells chronically exposed to lipids or fatty acids. During autophagosome formation, phosphatidylethanolamine is conjugated to cytosolic LC3 (LC3-I) to form LC3-II, which is sequestered in autophagosome membranes. LC3 serves as a marker for autophagosome content. Thus, in a functional cell, acidification of the lysosome results in fusion with the autophagosome, that allows for degradation of the autophagosomes and its contents, including LC3-II. Impaired lysosomal acidification reduces the degradation of autophagosomes. Fusion, thus, leads to accumulation of LC3-II. To deduce the effect on autophagic flux, two tests were applied. First is the measurement of p62 which was degraded in the autophagosome. Second, completely blocking the degradation of autophagosomes allowed for the estimation of any impact on autophagosome formation (measurement of LC3-II). To test the capacity of acNPs to prevent the accumulation of dysfunctional autophagosomes, cells were treated with acNPS during their entire 16-hour exposure to lipotoxicity. Chronic FA exposure resulted in increased LC3-II and p62 levels in the cell, and treatment with acNPs normalized the levels of these two proteins.

In another embodiment, the acNPs normalize protein and mitochondrial turnover in cells with lysosomal dysfunction. One can quantify the impact of acNPs on the specific outcomes of autophagy by measuring protein turnover and mitochondrial turnover—Two key physiological roles of autophagy are the turnover of protein and mitochondria. Mitochondrial turnover was determined using the probe, Fis1-GFP-mCherry (Addgene plasmid deposited by Dr. Anne Burnet), which monitors the rate of mitophagy in cells. Fis1-GFP-mCherry reports on mitochondria entering an acidic autophagosome upon which the fluorescence is quenched.

Mitochondrial protein turnover is measured using the probe, MitoTimer (Addgene plasmid deposited by Dr. Roberta Gottlieb), and is strongly influenced by the inhibition of the lysosomal proton pump with bafilomycin (32). Mitotimer changes emission spectra (from green to red) based on the age of the protein. Higher red/green fluorescence ratio during constitutive expression indicates accumulation of old protein within the mitochondria and is interpreted as a failure to effectively clear mitochondria via autophagy.

To determine the effect of acNPs on autophagy, INS1 cells and HepG2 cells can be treated with excess lipids, followed by acNPs incubation in the presence or absence of protease inhibitors, e.g., pepstatin+E64D. Protease inhibitors prevent degradation of autophagosome contents. We believe that reduced lysosomal acidification caused by chronic FA exposure will increase the ratio of red/green MitoTimer protein in β-cells and hepatocytes. Rescue of autophagic flux with acNPs will recover mitophagy and normalize red/green fluorescence in cells treated with FA.

Pharmacological inhibition of lysosomal acidification in vivo results in fatty liver, and inhibition of autophagy impairs glucose-stimulated insulin secretion. To date, it is not known whether increasing acidification is able to reverse fatty liver and insulin resistance (IR). Without being bound to a particular theory, we believe that restoration of lysosomal acidity and autophagic flux will normalize hepatocyte lipid content and enhance β-cell capacity to secrete insulin in response to glucose.

Autophagy consumes lipid droplets in a process termed lipophagy and accumulation of lipid droplets within hepatocytes plays a causal role in the development of insulin resistance (IR). In one aspect of the invention, activation of autophagy with acNPs reduced the lipid burden on hepatocytes by increasing lipophagy. In another embodiment, acNP treatment of a subject with lysosomal dysfunction as a result of excess FA exposure increased phosphorylation of protein kinase B (Akt). Protein kinase B (Akt) is directly phosphorylated by PI3K in response to stimulation of the insulin receptor. Phosphorylation of Akt occurs at Ser473. In states of insulin resistance (IR), phosphorylation of Ser473 is diminished as a result of FA exposure inducing IR. In another embodiment, acNPs restored insulin inhibitory effect on glucose production in insulin resistant hepatocytes.

The capacity of insulin to reduce glucose production by hepatocytes is diminished in obese, insulin resistant humans and is strongly correlated to hepatic lipid accumulation. To determine if acNPs are capable of restoring insulin inhibitory effect on glucose production in insulin resistant hepatocytes, hepatocytes are isolated and chronically cultured in FA in the presence or absence of acNPs.

In one aspect of the invention, acNPs treatment of cells exposed to excess lipid environment restored acidification over a long-term, leading to complete and sustained recovery of glucose-stimulated insulin secretion in the cells. In one embodiment, the defect in glucose-stimulated insulin secretion was prevented in a mammal exposed to excess lipid by administering to the mammal an effective amount of acNPs.

In one aspect of the invention, acNPs comprises a polymer of different polyester compositions. In one embodiment, the acNPs comprises a polyester wherein the chain length of the diol is varied. The polyester having diol of different chain length is selected from the group consisting of ethylene glycol, propylene glycol, butylene glycol, hexanediol, poly-ethylene glycol.

In another embodiment, the polyester is a linear or branched hydrocarbon of different chain length. In another embodiment, the acNPs comprise varying ratios of tetrafluorosuccinic acid (TFSA) to succinic acid (SA). The ratio of TFSA to SA is selected from the group consisting of about 10:90, about 15:85, about 20:80, about 25:75, about 30:70, about 35:65, about 40:60, about 45:55, about 50:50, about 55:45, about 60:40, about 65:35, about 70:30, about 75:25, about 80:20, about 15:15, about 90:10, about 95:5, and about 100:0.

In one aspect of the invention, pharmaceutical formulations comprising acNP and methods of use thereof are provided.

In view of the foregoing and the examples provided herein, one of skill will recognize that we have synthesized novel biodegradable acid-activated acid releasing nanoparticles (acNPs) to strategically target and manipulate lysosomal acidity and autophagy. These acNPs are degraded at pH 6.0 (pH reported in dysfunctional lysosomesto release component acids that further lower the lysosomal pH, thereby increasing autophagic flux and cellular function of hepatocytes under LT. The acNPs are useful as a therapeutic agent in restoring lysosomal function in individuals diagnosed with NAFLD or other lysosomal dysfunction diseases.

EXAMPLES

The following examples are offered to illustrate, but not to limit the claimed invention.

Example 1

Biodegradable Polyesters Modulate Lysosomal Acidification in Cells Under Lipotoxicity Synthesis of Library of Polyesters.

Poly-condensation was used in the preparation of the polyesters, with slight changes in reaction temperature and time based on the ratio of TFSA:SA. Polyesters with a TFSA:SA ratio larger than 50% were reacted at 130° C. versus 150° C. for the other polyesters. The polymer compositions, molecular weights and PDIs were characterized using $^1$H NMR, $^{13}$C NMR, $^{19}$F NMR (SI) and gel permeation chromatography (GPC) (FIGS. 2A-2E). The results from the NMR spectra confirmed the polyester composition and was in agreement with the theoretical ratio. Molecular weights are in the same order for the same series.

Thermal Properties of Polyesters

Figure 3C:
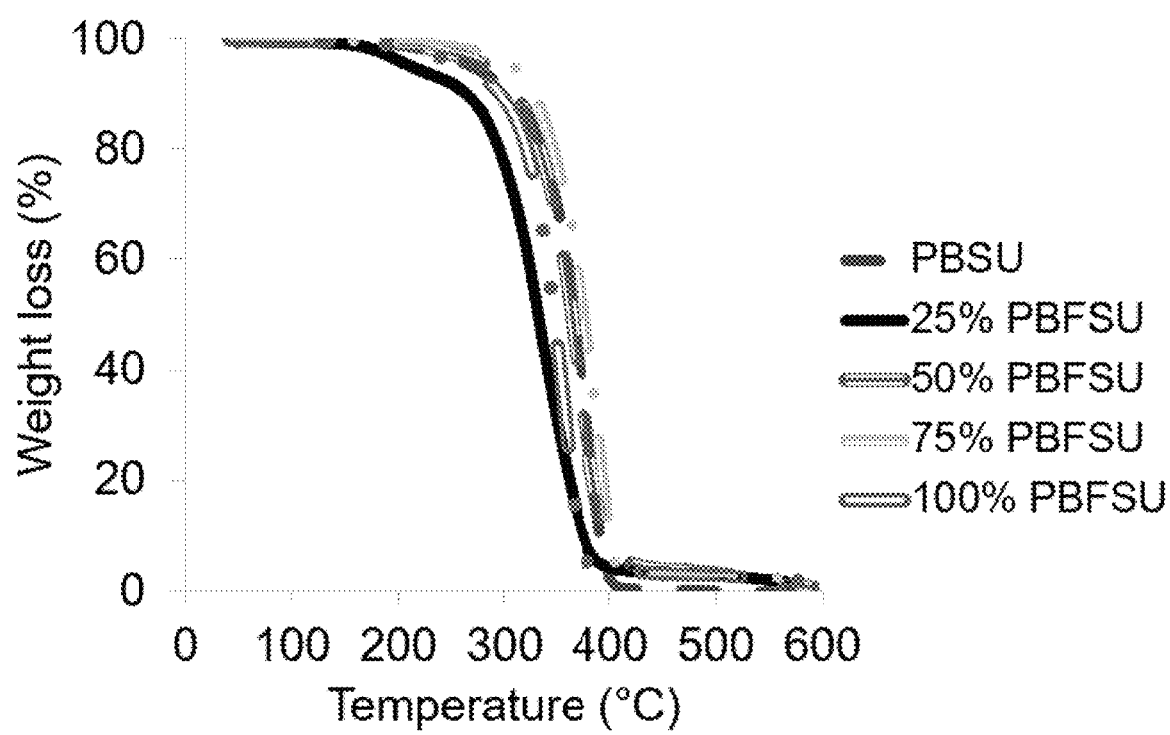
FIG. 3C: Thermogravimetric analysis (TGA) curves for the PBFSU polyesters. Control polymer was PBSU.

The thermal behavior of the polyesters was characterized with differential calorimetric scanning (DSC) and thermogravimetric analysis (TGA). The melting temperature, crystallization temperature and glass transition temperature, and the temperature at which the polyesters show 5% degradation ($T_{d, 5\%}$) or maximum degradation ($T_{d, max}$), were determined and the results are shown in Table 2. For many of the polyesters characterized, no melting temperature or crystallization point was detected. Most have a low glass transition temperature below −20° C. (FIGS. 3A and 3B). The results of this study indicate that the polyesters are mostly amorphous. The glass transition temperature decreased with increasing ratios of TFSA:SA used. All the synthesized polyesters showed no decomposition up to 250° C. (FIG. 3C).

Table 2 below shows the thermal properties of the synthesized polyesters. $T_g$ indicates transition temperature, $T_{cc}$: cold crystallization temperature, $\Delta H_{cc}$: heat flow changes during cold crystallization, $T_m$: melting temperature, $\Delta H_m$: heat flow changes during melting, $T_c$: crystallization temperature, $\Delta H_c$ heat flow changes during crystallization, $T_{d,5\%}$: temperature at which polyester shows 5% decomposition, and $T_{d,max}$: temperature at which the polyester shows maximum decomposition.

generating acNPs. Nanoparticle formation depends on the particle nucleation, molecular growth, and aggregation. In brief, nanoparticles were formed by first dissolving the polymer in a water miscible solvent (i.e., acetone/DMF), and added dropwise via a 25 G syringe needle in a fast stirring aqueous solution with different types of surfactants. The organic solvent and excess surfactants were removed by dialyzing over time. To obtain acNPs having different sizes and stability, several parameters were varied, e.g., (1) type and amount of polymer, (2) type of organic solvent, (3) solvent to aqueous solution ratio, (4) type of surfactant, (4) polymer to surfactant ratio, (5) dialysis time and (6) temperature (Table 3). The size, morphology and stability of the acNPs were characterized by dynamic light scattering (DLS), scanning electron microscopy (SEM) and Zeta Potentializer. (FIG. 4) shows the SEM images of representative acNPs formulated using the different polymers that were synthesized with butylene glycol (polyester) and TFSA:SA ratios.

Effect of Solvent Type

Figure 5:
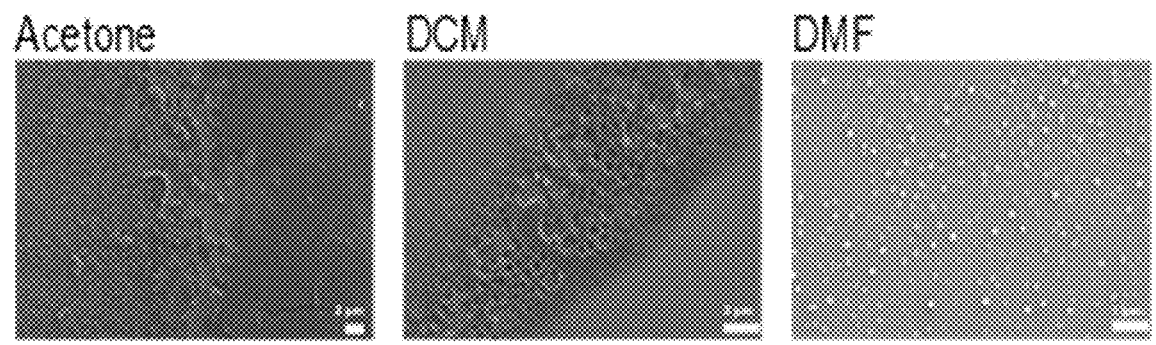
FIG. 5 shows the effects of solvents on acNPs formation.

To explore the different variables used to form acNPs, 50% PBFSU was chosen as the model polymer. Different solvents were used in the preparation of the acNPs. Among the solvents used were acetone, dichloromethane (DCM) and dimethylformamide (DMF). acNPs formed from DMF were the most spherical and had the lowest polydispersity (0.125), which indicates high stability. The acNPs size were also small—133.9 nm. Although Table 3 indicates that acNPs synthesized from acetone were even smaller, the SEM images (FIG. 5) revealed excess surfactants and uneven morphology, indicating incomplete particle formation (SI).

TABLE 2

| | Heating Scan (10° C./min) | | | | Cooling Scan | | | |
|---|---|---|---|---|---|---|---|---|
| Polymer | $T_g$ (° C.) | $T_{cc}$ (° C.) | $\Delta H_{cc}$ (W/g) | $T_m$ (° C.) | $\Delta H_m$ (W/g) | $T_c$ (° C.) | $\Delta H_c$ (W/g) | $T_{d, 5\%}$ (° C.) | $T_{d, max}$ (° C.) |
| 25% PBFSU | — | — | — | 84.6 | 0.75 | 31.0 | 0.25 | 225 | 300 |
| 50% PBFSU | −46.0 | — | — | — | — | — | — | 290 | 325 |
| 75% PBFSU | −51.7 | — | — | — | — | — | — | — | — |
| 100% PBFSU | −53.9 | — | — | — | — | — | — | 270 | 330 |
| PBSU | — | 98.7 | 0.5 | 115.3 | 2.5 | 80.3 | 1.00 | 275 | 350 |

Synthesis of Mono-Disperse Nano-Sized acNPs.

The polyesters were characterized for their ability to form nanoparticles. Methods of making nanoparticles include but are not limited to mini-emulsion, sonication[12], solvent displacement, and nanoprecipitation. Nanoprecipitation is a simple, fast method that allows the use of non-highly toxic solvents without any high shear stress. Furthermore, the method allows easy scale up to industrial magnitude for

TABLE 3

Effect of formulation variables on the formation of acNPs.

| Polymer used | Sol[a] | Aq[b] | Polymer Conc[d] [mg/mL] | Surf[c] | Surf Conc. [mg/mL] | Sol. to Aq. | Polymer to Surf. | T[e] [° C.] | Time [Hrs] | Diameter [nm] | PDI[f] | Zeta Potential (mV) |
|---|---|---|---|---|---|---|---|---|---|---|---|---|
| Effect of solvent type | | | | | | | | | | | | |
| 50% PB | Acetone | DI | 0.5 | SDS | 2.0 | 1:10 | 1:4 | 25 | 24 | 105.9 ± 9.05 | 0.244 ± 0.04 | −46.28 |
| 50% PB | DCM | DI | 0.5 | SDS | 2.0 | 1:10 | 1:4 | 25 | 24 | 31347 ± 9990 | 0.411 ± 0.31 | −10.36 |
| 50% PB | DMF | DI | 0.5 | SDS | 2.0 | 1:10 | 1:4 | 25 | 24 | 103.3 ± 1.76 | 0.227 ± 0.03 | −29.42 |
| Effect of surfactant type | | | | | | | | | | | | |
| 50% PB | DMF | DI | 0.5 | SDS[h] | 2.0 | 1:20 | 1:4 | 25 | 24 | 80.9 ± 6.71 | 0.220 ± 0.07 | −22.20 |
| 50% PB | DMF | DI | 0.5 | PVA[i] | 2.0 | 1:20 | 1:4 | 25 | 24 | 406.1 ± 4.25 | 0.251 ± 0.053 | −10.01 |
| 50% PB | DMF | DI | 0.5 | F127[k] | 2.0 | 1:20 | 1:4 | 25 | 24 | 303.3 ±= 3.21 | 0.317 ± 0.123 | −6.84 |
| Effect of polymer to surfactant ratio | | | | | | | | | | | | |
| 50% PB | DMF | DI | 4.0 | SDS | 2.5 | 1:10 | 8:5 | 25 | 24 | 175.0 ± 16.8 | 0.150 ± 0.06 | −21.95 |
| 50% PB | DMF | DI | 3.0 | SDS | 2.5 | 1:10 | 6:5 | 25 | 24 | 147.2 ± 21.2 | 0.156 ± 0.02 | −20.79 |
| 50% PB | DMF | DI | 1.0 | SDS | 2.5 | 1:10 | 2:5 | 25 | 24 | 110.8 ± 9.12 | 0.213 ± 0.05 | −28.55 |

TABLE 3-continued

Effect of formulation variables on the formation of acNPs.

| Polymer used | Sol[a] | Aq[b] | Polymer Conc[d] [mg/mL] | Surf[c] | Surf Conc. [mg/mL] | Sol. to Aq. | Polymer to Surf. | T[e] [° C.] | Time [Hrs] | Diameter [nm] | PDI[f] | Zeta Potential (mV) |
|---|---|---|---|---|---|---|---|---|---|---|---|---|
| 50% PB | DMF | DI | 2.0 | SDS | 8.0 | 3:20 | 1:4 | 25 | 24 | 110.8 ± 20.2 | 0.140 ± 0.03 | −33.19 |
| 50% PB | DMF | N[g] | 2.0 | SDS | 8.0 | 3:20 | 1:4 | 25 | 24 | 100.7 ± 1.20 | 0.120 ± 0.03 | −31.40 |
| 50% PB | DMF | DI | 2.0 | SDS | 20.0 | 1:10 | 1:10 | 25 | 24 | 158.0 ± 9.05 | 0.171 ± 0.01 | −36.91 |
| 50% PB | DMF | DI | 0.2 | SDS | 2.0 | 1:10 | 1:10 | 25 | 24 | 21899 ± 10770 | 1.219 ± 0.423 | N/A |
| 50% PB | DMF | DI | 0.50 | SDS | 20.0 | 1:10 | 1:40 | 25 | 24 | 144.0 ± 18.7 | 0.252 ± 0.08 | −35.22 |
| Effect of dialysis temperature | | | | | | | | | | | | |
| 50% PB | DMF | DI | 0.50 | SDS | 2.0 | 1:20 | 1:4 | 0 | 24 | 82.3 ± 16.3 | 0.244 ± 0.02 | −31.55 |
| 50% PB | DMF | DI | 0.50 | SDS | 2.0 | 1:20 | 1:4 | 25 | 24 | 80.9 ± 6.71 | 0.220 ± 0.07 | −34.71 |
| Effect of dialysis time | | | | | | | | | | | | |
| 50% PB | DMF | DI | 0.50 | SDS | 2.0 | 1:20 | 1:4 | 25 | 24 | 87.9 ± 3.74 | 0.210 ± 0.01 | −30.71 |
| 50% PB | DMF | DI | 0.50 | SDS | 2.0 | 1:20 | 1:4 | 25 | 36 | 92.5 ± 3.89 | 0.237 ± 0.05 | −18.37 |
| Effect of polymer type | | | | | | | | | | | | |
| PBSU | DMF | N. | 2.0 | SDS | 8.0 | 3:20 | 1:4 | 25 | 24 | 120.3 ± 32.1 | 0.202 ± 0.021 | −28.21 |
| 25% PB | DMF | N. | 2.0 | SDS | 8.0 | 3:20 | 1:4 | 25 | 24 | 150.0 ± 13.2 | 0.208 ± 0.01 | −31.20 |
| 50% PB | DMF | N. | 2.0 | SDS | 8.0 | 3:20 | 1:4 | 25 | 24 | 100.7 ± 1.20 | 0.120 ± 0.03 | −31.40 |
| 75% PB | DMF | N. | 2.0 | SDS | 8.0 | 3:20 | 1:4 | 25 | 6 | 110.7 ± 22.7 | 0.147 ± 0.03 | −29.72 |
| 100% PB | DMF | N. | 2.0 | SDS | 8.0 | 3:20 | 1:4 | 25 | 6 | 129.5 ± 20.2 | 0.164 ± 0.03 | −35.32 |

Legend:
[a]Solvent type,
[b]aqueous type,
[c]surfactant type,
[d]concentration,
[e]temperature,
fpolydispersity,
[g]nanopure ultra-filtered water,
[h]sodium dodecyl sulfate,
[i]poly vinyl alcohol,
[j]poly-L-lysine and
[k]pluronic F127.

Effects of Surfactant Type

After determining the type of solvent used, the effect of different surfactants on acNPs formation were considered. Nanoparticles made with sodium dodecyl sulfate (SDS) generated the smallest diameter and PDI, while that of poly-L-lysine resulted in a size one order of magnitude greater than that obtained using SDS, and with significant aggregation. The two non-ionic surfactants, polyvinyl alcohol (PVA) and pluronic F127, also generated significantly larger nanoparticles than SDS.

Effects of Polymer to Surfactant Ratio

The polymer to surfactant ratio was determined by varying the final concentration in mg/mL of the polymer in DMF and the surfactant in Nanopure water. Formulations were conducted in which the concentration of the surfactant was (1) greater than, (2) equal to, or (3) less than the concentration of polymer used. The optimal ratio for acNP formation was found to be 1:4 (i.e., a 1 mg/mL final concentration of 50% PBFSU: 4 mg/mL of SDS). Subsequent formulations kept the solvent-to-aqueous ratio constant, the polymer-to-surfactant ratio at 1:4, with a single parameter varied to determine the effects of these parameters.

Effects of Solvent to Aqueous Ratio

A lower solvent to aqueous ratio resulted in the formation of much smaller nanoparticles.

Effects of Dialysis Temperature

Figure 6:
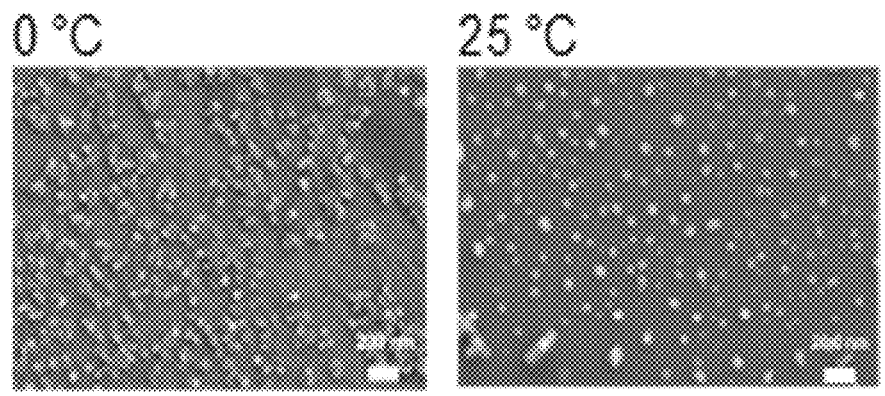
FIG. 6 shows the effects of dialysis temperatures on acNPs formation.

When the polymer to surfactant ratio and solvent to aqueous ratio were fixed, the dialysis temperature and time were determined. acNPs formation were tested at either 0° C. or 25° C. This is because temperature manipulation affects the critical micelle concentration (CMC) of surfactants, where CMC usually decreases with temperature increase until a certain point at which an increase in temperature then corresponds to an increase in CMC. At 0° C., the CMC of SDS in water was 2.75 mg/mL while at 25° C., the CMC fell within the range of 2.30-2.50 mg/mL. acNP formulations were tested at both 0° C. and 25° C. with varying concentrations of SDS above and below the CMC. Optimal nanoparticles were formed at concentrations of SDS above the CMC at 25° C. SEM images show that under this condition, the acNPs formed were spherical and had a disperse population (FIG. 6). At 0° C., the size, polydispersity and zeta potential were similar to that obtained at 25° C. Higher temperatures that are greater than the room temperature of 25° C. were not tested due to the volatility of DMF. In addition, dialysis at high temperatures resulted in a decrease in the CMC, reducing the surfactant's ability to encapsulate the polymer, which was hindered because of rapid micelle formation.

Effects of Dialysis Time

Figure 7:
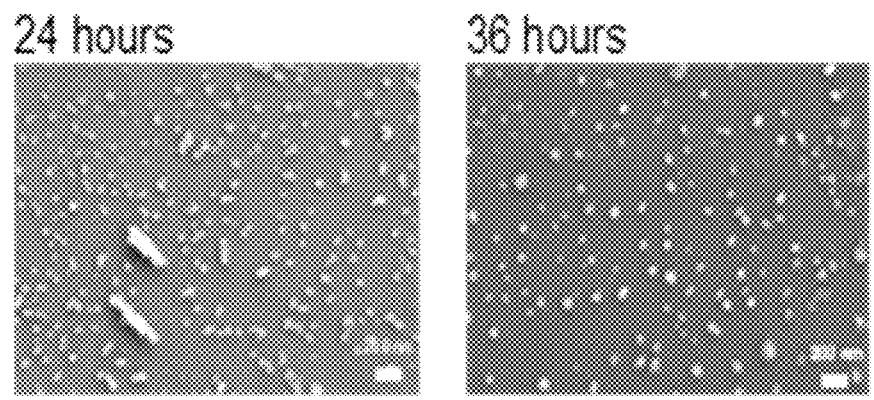
FIG. 7 shows the effects of dialysis time on acNPs formation.

The dialysis time was found to significantly affect the nanoparticle size. Comparing the time points between 24 and 36 hours, a 24-hour dialysis time yielded nanoparticles with optimal size and stability. When dialysis time increased to 36 hours, the size of acNPs did not change significantly (FIG. 7).

Effects of Polymer Type

The type of polymer used affects the dialysis time required to form the acNPs. acNPs with a lower TFSA:SA content or a shorter glycol length required a shorter dialysis time—i.e., 75% PBFSU and 100% PBFSU needed only 6 hours of dialysis (the average diameter of the acNPs formed is 94.6 nm, with PDI of 0.124), and with 25% PEFSU only 8 hours of dialysis was needed. On the other hand, 25%

Figure 4:
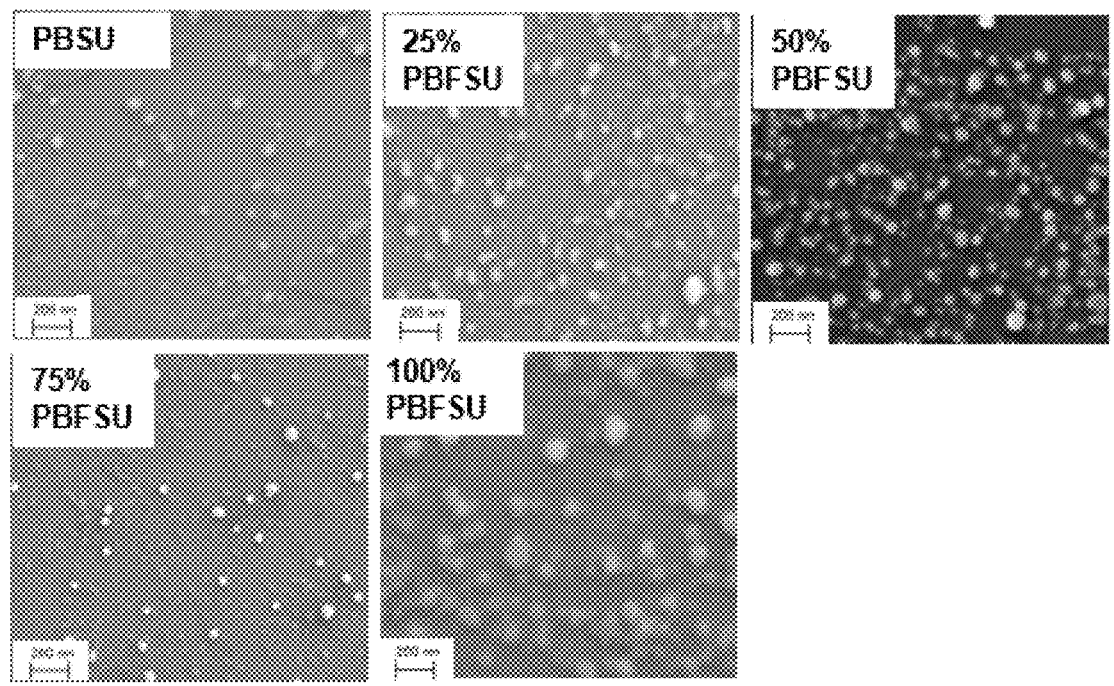
FIG. 4 SEM images of PBFSU acNPS.

PBFSU or 50% PBFSU required 24 hours for acNPs formation (average diameter 133.9 nm, PDI 0.125). The acNPs formation is characterized using both DLS and SEM imaging (FIG. 4).

Characterization of Degradation Rate of acNPs via pH and GPC Analysis

Figure 8A:
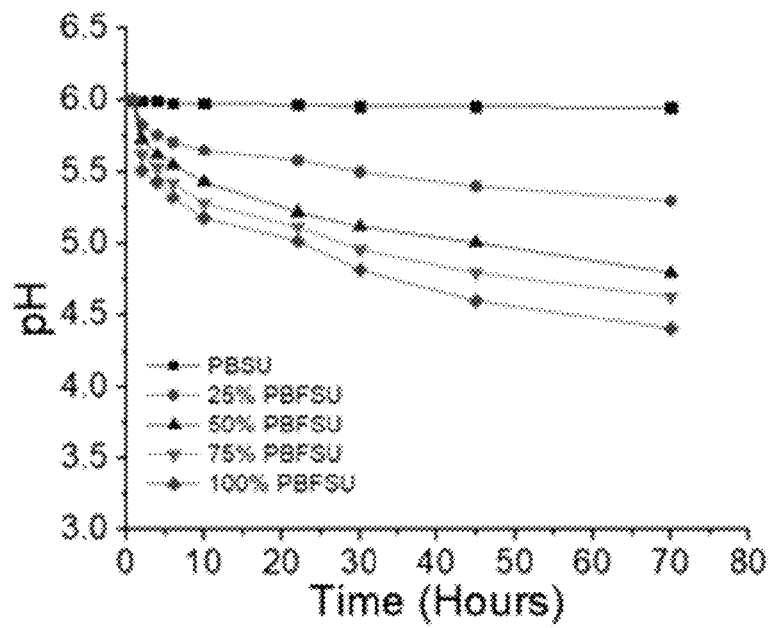
FIG. 8A shows the effect on pH changes over time when different PBFSU acNPs were incubated in 20 mM PBS at pH 6.
Figure 8B:
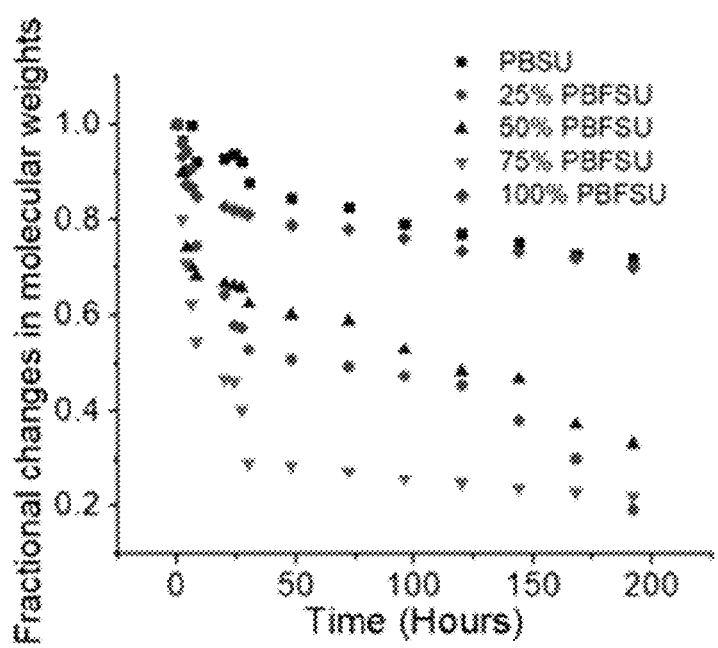
FIG. 8B shows the degradation and molecular weight changes of PBFSU acNPs when the nanoparticles were incubated in water at 37° C.

The pH modulating ability and degradation rate in different types of buffering environment were studied using the synthesized acNPs described above. The acNPs were suspended in either DI water, or 20 mM PBS buffer of pH 6.0 over time and both the changes in pH and molecular weight were measured. 20 mM PBS buffer pH 6.0 was chosen because it simulated the buffering capacity of dysfunctional lysosomes of 19±6 mmol/Ph. At pH 6.0, ethylene glycol containing polyesters had acidified faster compared to butylene glycol containing polyesters (FIG. 13B). Comparing the acNPs in the same series, i.e., PBFSU acNPs, PBFSU acNPs having a higher TFSA:SA ratio showed greater acidification rates (FIGS. 8A and 8B).

The degradation rates of the acNPs were measured by determining the rate of decrease in molecular weight of the polymer in water at 37° C. using gel permeation chromatography (GPC). acNPs were suspended in water and incubated for 1 h, 2 h, 4 h, 6 h, 12 h, 24 h, 48 h, 72 h, 1 week, 2 weeks at 37° C. At each specified time-point, an aliquot of the polymer solution was collected, dried and re-dissolved in tetrahydrofuran (THF) solvent before analysis using GPC. FIG. 8B shows that the acNPs degraded at a steady rate, indicating that degradation occurred from the end groups, rather than from the center. Within the PBFSU series, the higher the TFSA:SA ratio, the slower the degradation rate.

Comparing acNPs prepared using different polyesters, the polyesters having a shorter glycol chain experienced faster degradation. Based on the degradation curves, the PBFSU polyesters underwent a heterogeneous biphasic degradation. In the first phase (0-24 hours), the PBFSU ester bonds were hydrolyzed throughout slowly. In the second phase (24-48 hours), the carboxylic acid end groups of the degradation products (i.e., TFSA or SA) lowered the pH and catalyzed further degradation of the interior of the nanoparticles. This allowed for faster water penetration and massive loss of the nanoparticles as seen by an increased degradation rate.

Cytotoxicity of the acNPs and Lysosomal pH Restoration Capacity with acNPs.

Figure 9A:
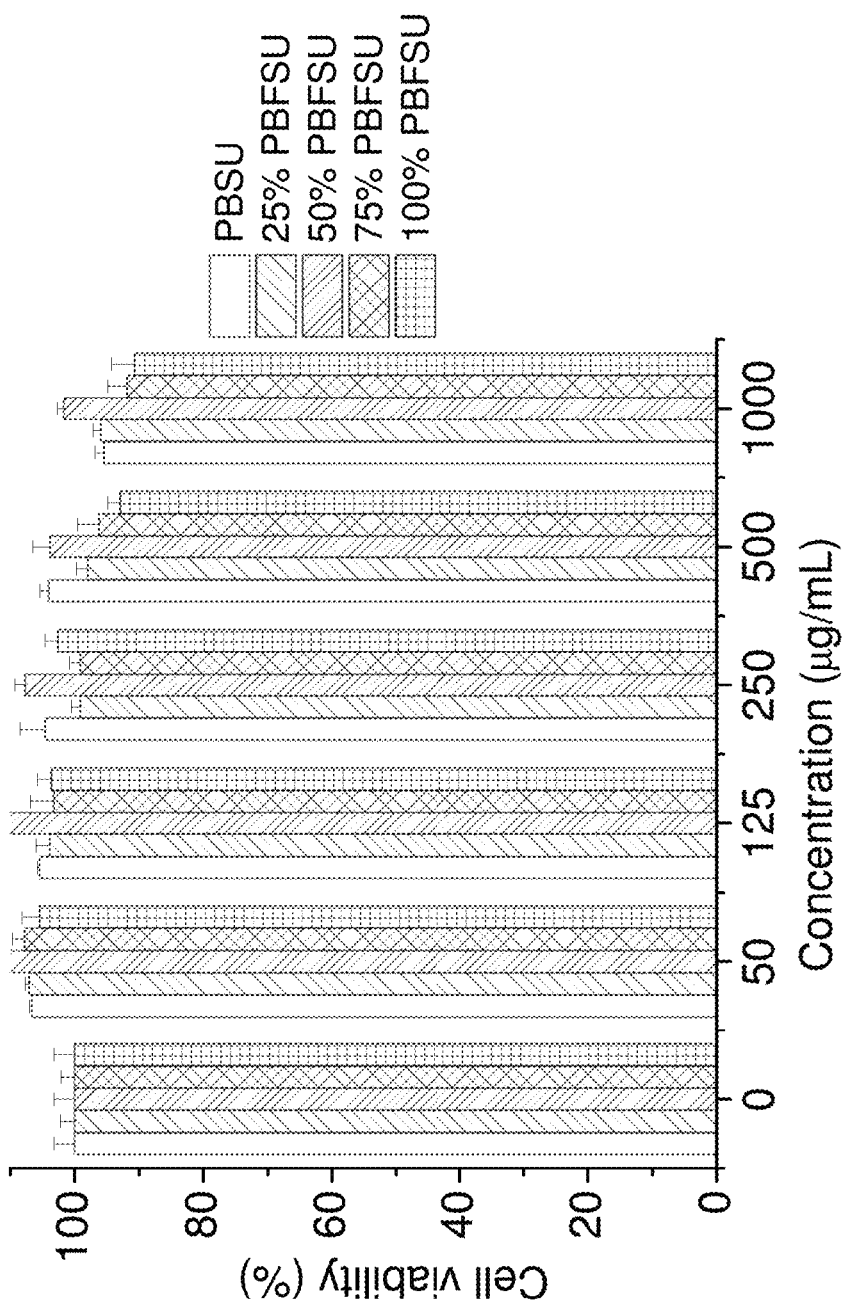
FIGS. 9A and 9B: Cytotoxicity assays of acNP. PBFSU acNPs do not induce significant cell death even at 1000 μg/mL.
Figure 9B:
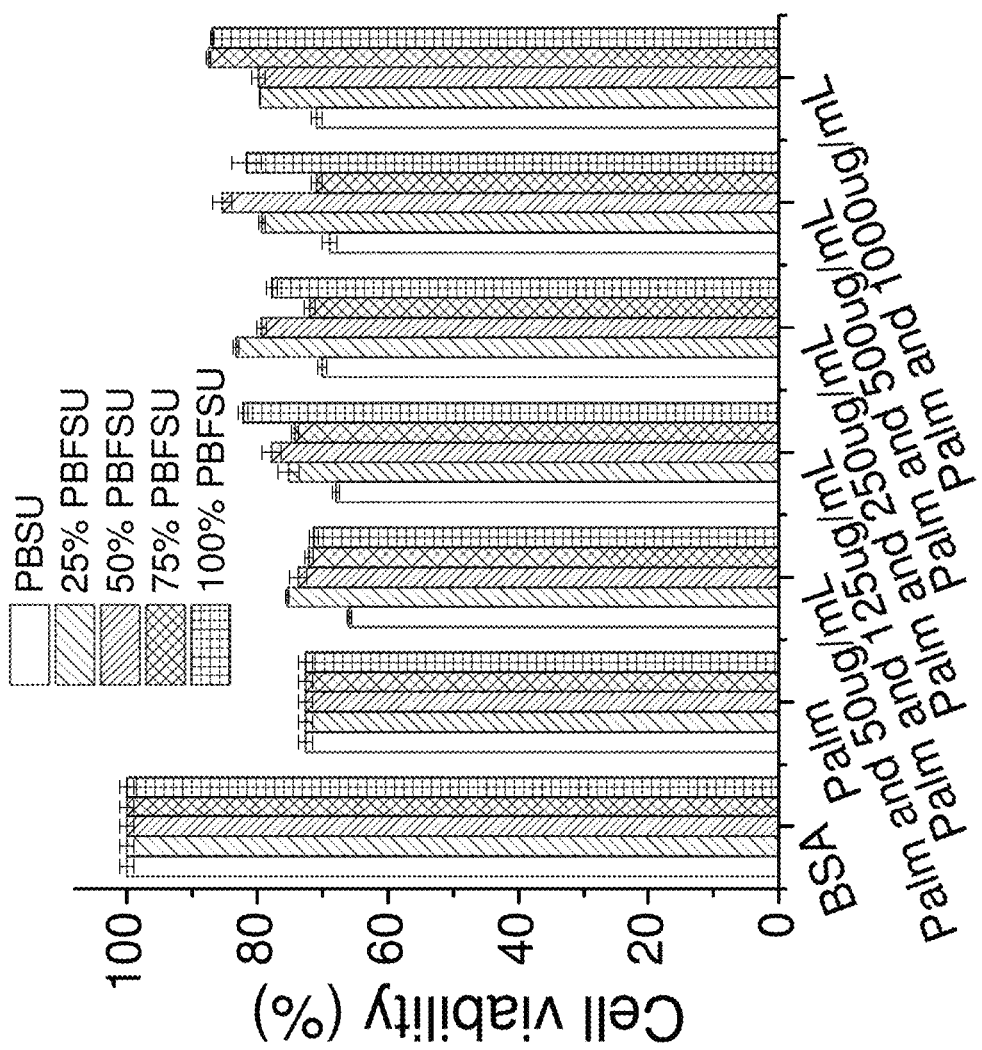

The cytotoxicity of the PBFSU acNPs was determined in the HepG2 cell line. No significant deaths were observed when HepG2 cells were incubated with acNPs prepared using different polymers: TFSA/SA ratios at a concentration up to 1000 μg/mL (FIG. 9A). The ability of the PBFSU acNPs to rescue palmitate induced cell death was determined. (FIG. 9B). It was found that the acNPs that have a higher acid release rate and released amount were able to increase cell viability.

Furthermore, the acNPs were tested for their ability to modulate lysosomal pH in HepG2 cells under lipotoxicity conditions. The HepG2 cells were incubated with either (1) palmitate complexed to BSA (palmitate:BSA) for 16 hours to induce lipotoxicity or (2) palmitate:BSA with different acNPs (50%, 75% and 100% PBFSA acNPs) for 16 hrs. The lysosomal pH was assessed with LysoSensor™ yellow/blue dye and confocal imaging. MetaMorph analysis software was used to quantify the images (FIGS. 10A and 10B). Results showed that butylene based acNPs restored lysosomal pH within 16 hours of incubation, in line with their fast degradation kinetics.

Example 2

Degradable Acidic Nanoparticles Restore Lysosomal pH and Autophagic Flux in Cells Under Lipotoxicity Synthesis and Characterization of Biodegradable acNPs (PEFSU acNPs) and Their Degradation Kinetics in Solution.

Figure 11:
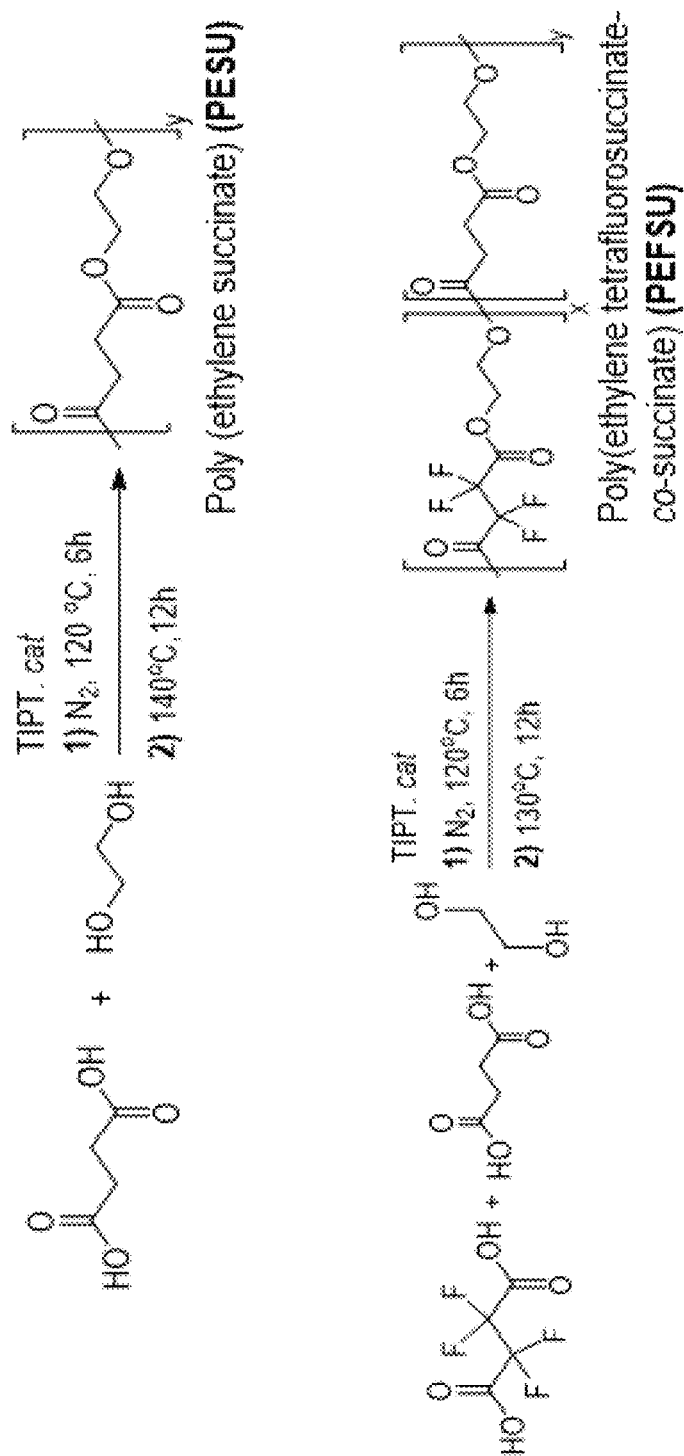
FIG. 11 illustrates the synthesis of acNP, PESU and PEFSU.

Acid-activated acidic nanoparticles were synthesized based on a series of synthesized poly(ethylene succinic-co-tetrafluorosuccinate) polymers (PESU and 25% PEFSU) that can biodegrade to release component carboxylic acids—tetrafluorosuccinic acid (TFSA) and succinic acid (SA) that significantly lowered surrounding pH (FIG. 11).

In general, polyesters do not readily hydrolyze in an aqueous environment at pH 7-7.4. However, in the presence of a slightly acidic environment (pH 6.0), they undergo hydrolysis, degraded, and released acid. The challenge lies in the additional lowering of surrounding pH upon hydrolysis and NP degradation. Previously synthesized biodegradable polyesters composed of acids such as glycolic acid or lactic acid, which have relatively high pKa values (e.g., glycolic acid=3.83, lactic acid=3.86) lower the pH only slightly. The polyester in the present invention incorporates TFSA, which has a much lower pKa of ~1.6. acNPs made from these TFSA/SU polyesters enable significant restoration of lysosomal pH by releasing stronger acid than PLGA nanoparticles synthesized from DL-lactide-co-glycolide.

acNP Acidification Capability.

Figure 12A:
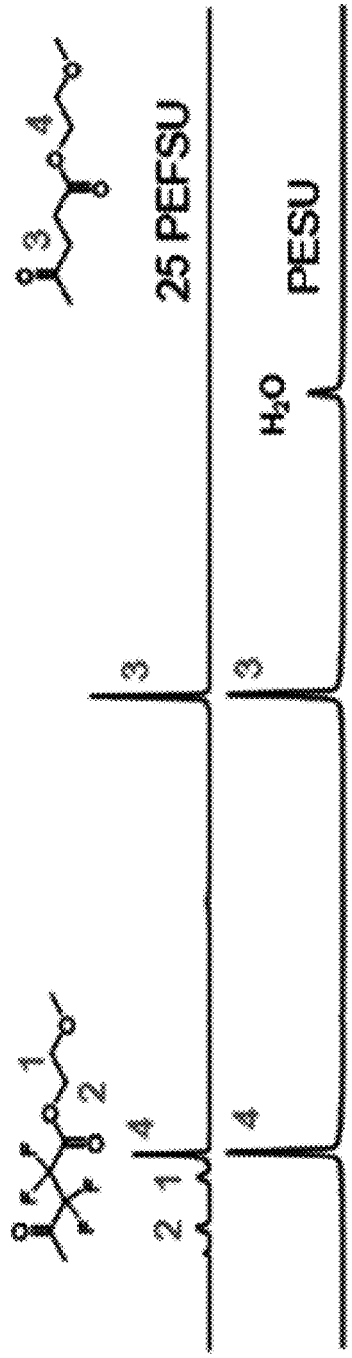
FIGS. 12A-12C show characterizations of PESU and 25% PEFSU using NMR spectra.
Figure 12B:
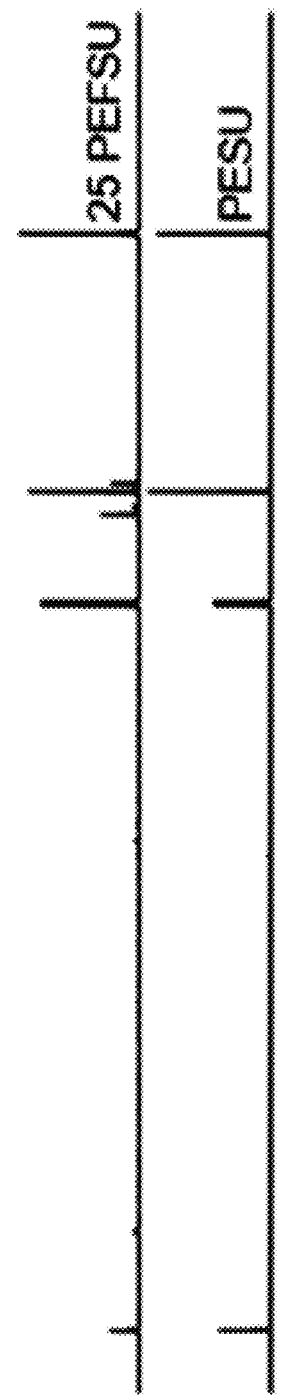
Figure 12C:

To demonstrate the acid releasing and pH lowering properties of these acNPs, two different polymers (PESU and 25% PEFSU) were synthesized by varying the ratio of TFSA and SA with different degradation and acid releasing rates. $^1$H, $^{13}$C and $^{19}$F NMR spectra and polymer characterizations are shown in FIGS. 12A-12C.

Figure 13A:
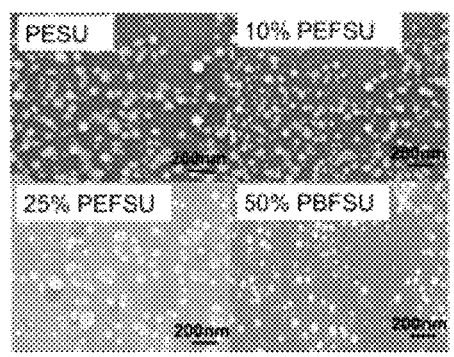
FIGS. 13A and 13B illustrate the characterization of acNPs' size and in vitro functionality.
Figure 13B:
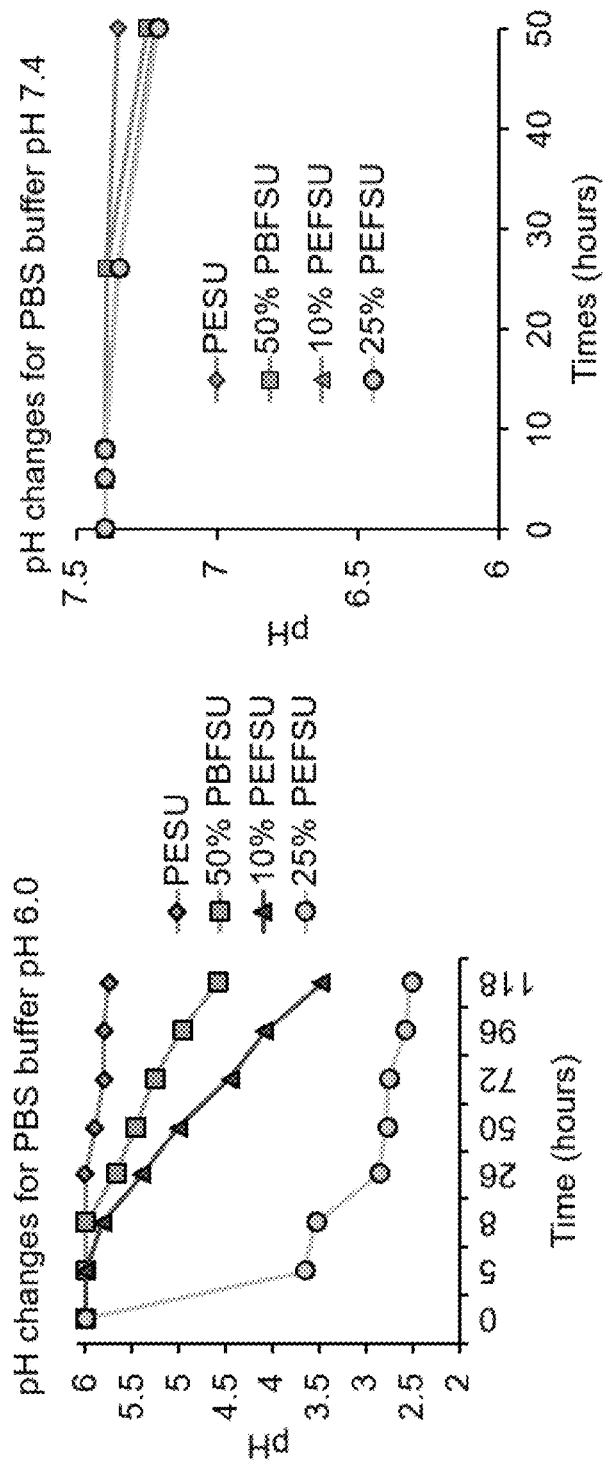

Illustrative results of acNPs formed from polyesters 10% PEFSU, 25% PEFSU, PESU and 50% PBFSU demonstrate relatively small size and uniform distribution (diameter<100 nm, PDI<0.14) according to dynamic light scattering and scanning electron microscopy studies (FIG. 4 (PBFSU), and FIG. 13A (PEFSU)).

Figure 14A:
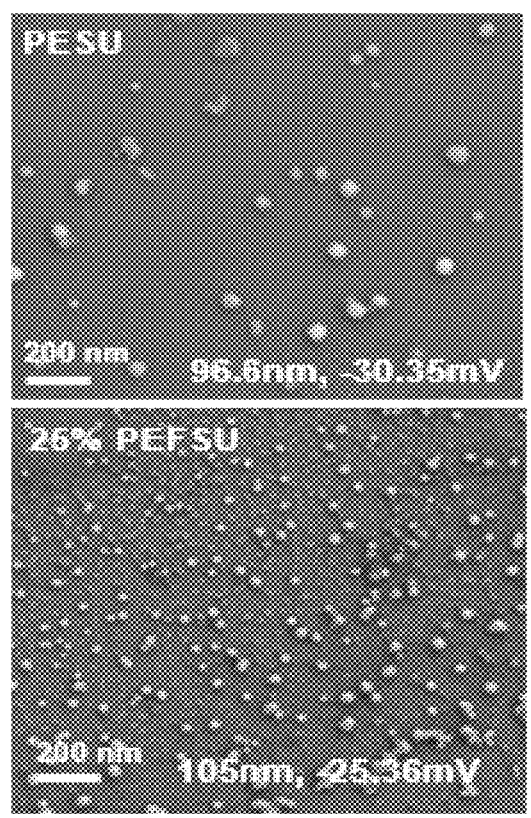
FIG. 14A: Characterization of acNP, PESU and and 25% PEFSU using dynamic light scattering to determine diameters and zeta potentials of the acNPs (size and zeta potential labelled on the SEM figures).
Figure 14B:
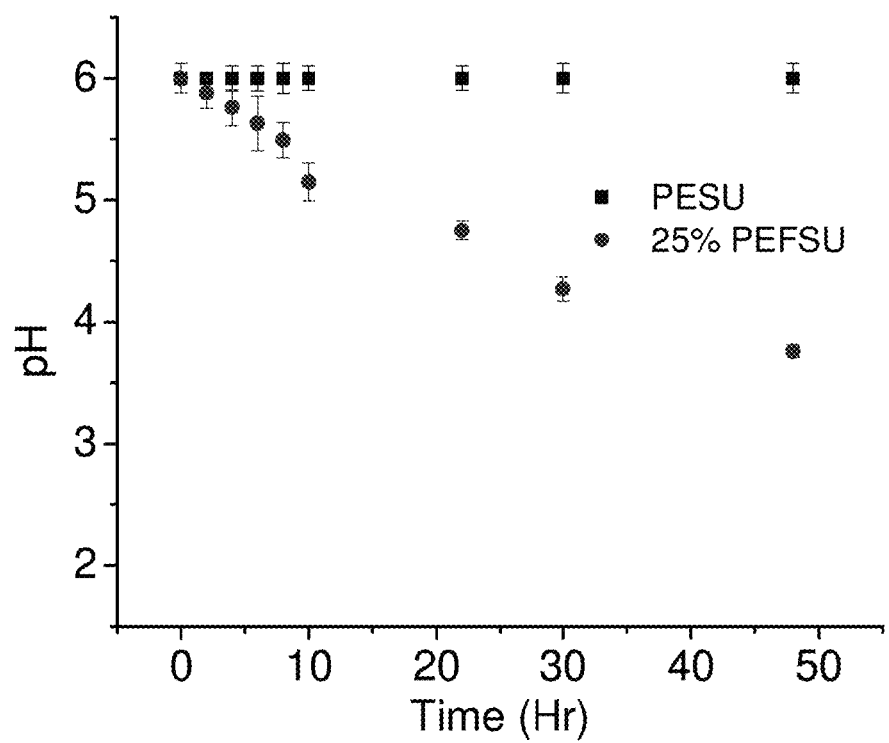
FIG. 14B: pH changes of acNPs in 20 mM pH 6.0 (top panel) and pH 7.4 (bottom panel) PBS buffers over a period of 48 hours.
Figure 14B:
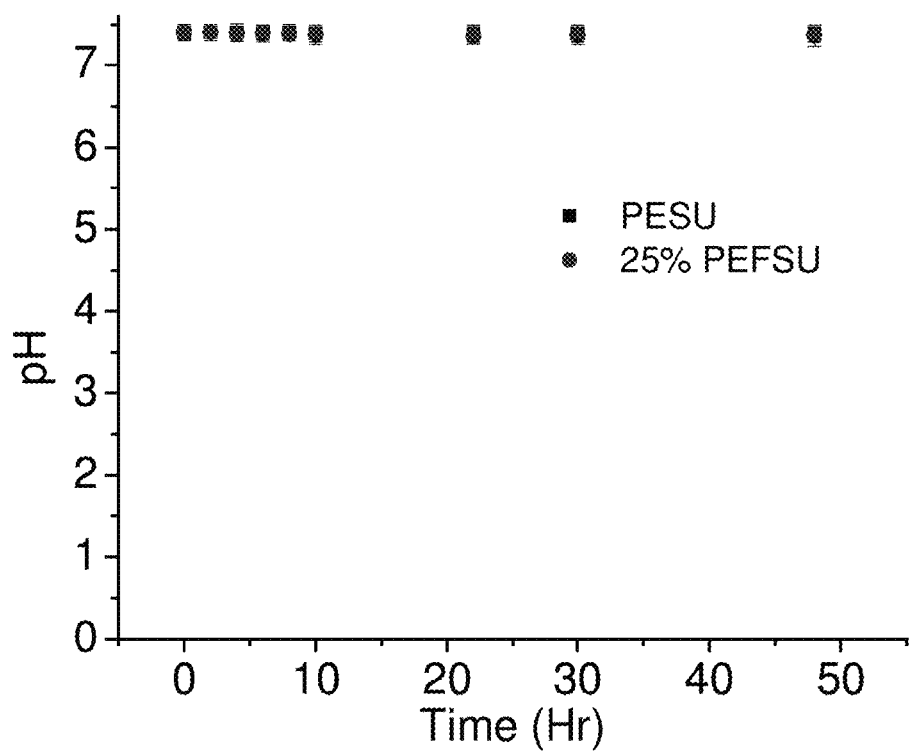

The rate and extent of acidification can be determined readily when acNPs are incubated in 20 mM PBS buffer of pH 6.0, 7.4 and 8.0, and DI water over time at both 25 and 37° C. The 20 mM PBS buffer pH 6.0 was chosen because it simulates the buffering capacity of dysfunctional lysosomes (19±6 mM, pH=6.0) (22). Additionally, the experiments are repeated in plasma at pH 7.4 as this is more representative of the in vivo plasma environment. acNPs that alter plasma pH need not be considered further as they are unlikely to be compatible with in vivo testing. Preliminary data show that acNPs composed of 25% PEFSU (25:75 TFSA:SA and ethylene glycol) when exposed to a pH 7.4 buffer did not change the pH, while in a pH 6.0 buffer the pH significantly decreased from 6 to 3 (FIG. 14B). In contrast, the acNP composed of polyester, 50% PBFSU (50:50 TFSA:SA and butylene glycol) resulted in a slower release of acid due to the greater hydrophobicity of the butylene glycol compared to ethylene glycol. (FIG. 13B). acNPs composed of 10% PEFSU (10% TFSA) degraded slower than 25% PEFSU due to a lower TFSA content which decreased its rate of acidification. (FIG. 13B). These results support our hypothesis. Hence, we believe that the degree of acidification can be finely controlled by changing the TFSA:SA ratio and type of glycol.

PESU containing 0% TFSA and 100% SA served as controls because they were expected to have a slow degradation rate and hence no significant change in pH. On the other hand, 25% PEFSU (25% TFSA and 0% SA) have increased TFSA content, which can increase their acidity and pH lowering properties. Monodisperse acNPs were formed using the synthesized polymers through a nanoprecipitation technique.[1] The size, morphology and stability of the acNPs were characterized by dynamic light scattering (DLS), scanning electron microscopy (SEM) and Zeta Potentializer respectively. (FIG. 14A). The acNPs formed have average diameters of 100 nm, and zeta potential between −25 to −30 mV, indicating good stability in solution (FIG. 14A).

Figure 15A:
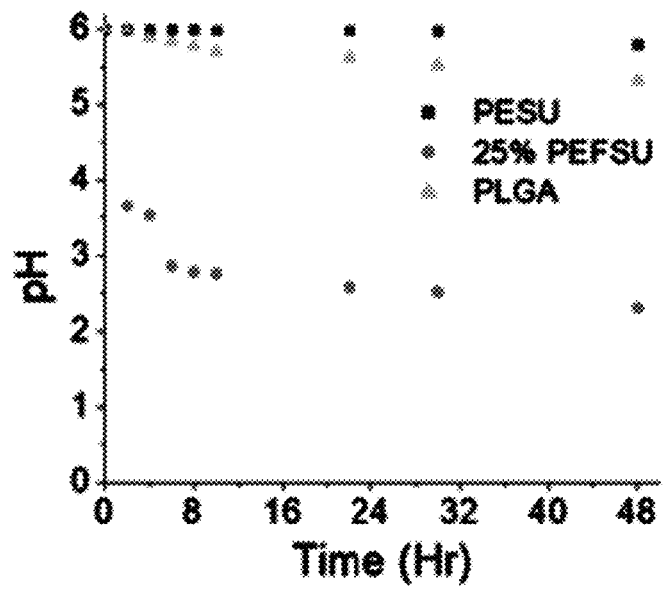
FIGS. 15A and 15B show pH changes of PESU, 25% PEFSU acNPs and PLGA NPs. Nanoparticles were incubated in a 20 mM pH 6.0 buffer (FIG. 15A) and 20 mM pH 7.4 buffer (FIG. 15B). 25% PEFSU acNPs show higher reduction of lysosomal pH (lower pH) compared to PLGA NPs.
Figure 15B:
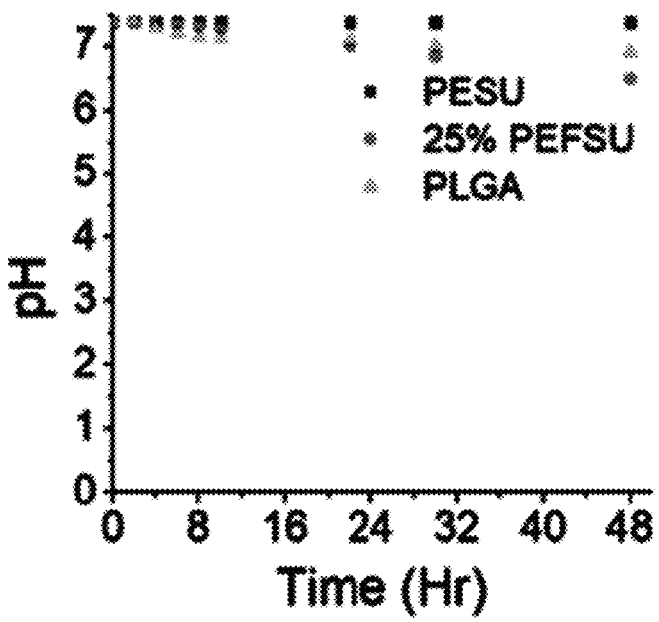

To determine the degree of acidification of the acNPs, pH changes in a suspension of acNPs in PBS pH 6.0 buffer (a lysosomal environment mimic buffer) and at pH7.4 over 48 hours were measured. In pH 6.0, 25% PEFSU based acNPs significantly acidified PBS pH buffer (20 mM) within the first 4 hours and continued acidification up to 24 hrs. (FIG. 13B and FIG. 14B, upper panel). In contrast, the PESU based acNPs did not result in pH changes, probably because of the slow degradation rate of the polymer and hence the low amount of succinic acid released, which did not have a significant effect on lowering the pH (FIG. 13B and FIG. 14B, upper panel). The pH release is also being compared with PLGA NPs that have been used for similar applications in other cell lines, showed a much slower rate of acid release than 25% PEFSU acNPs (FIGS. 15A and 15B).

Rate of acNPs Cellular Uptake and Localization to the Endosomal/Lysosomal Compartment Characterization of the Rate of Uptake of acNPs into Cells and Lysosomes.

Figures 16A, 16B:
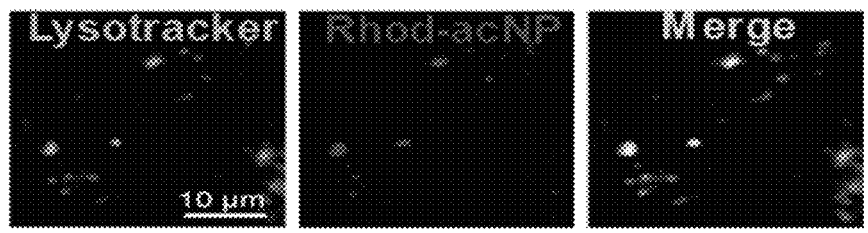
FIGS. 16A and 16B illustrate cellular uptake and localization of acNPs in lysosomes.

To visualize the route of acNPs uptake into cells and lysosomes, acNPs were covalently labeled with rhodamine (Rho-acNPs). HepG2 and INS1 cells were incubated with Rho-acNPs for 24 hours. LysoTracker Green DND-26, which labels lysosomes, were added to achieve a final concentration of 50 nmol/mL in the culture media at 30 minutes prior to confocal imaging (25, 26). Co-localization of the Rho-acNPs with Lysotracker green dye were quantified to determine if Rho-acNPs localized inside the lysosomes. Rho-acNPs (25% PEFSU) showed co-localization with Lysotracker green dye, indicating uptake into lysosomes (see, e.g., FIG. 16A).

Cytotoxicity and Uptake of acNPs.

Figure 17A:
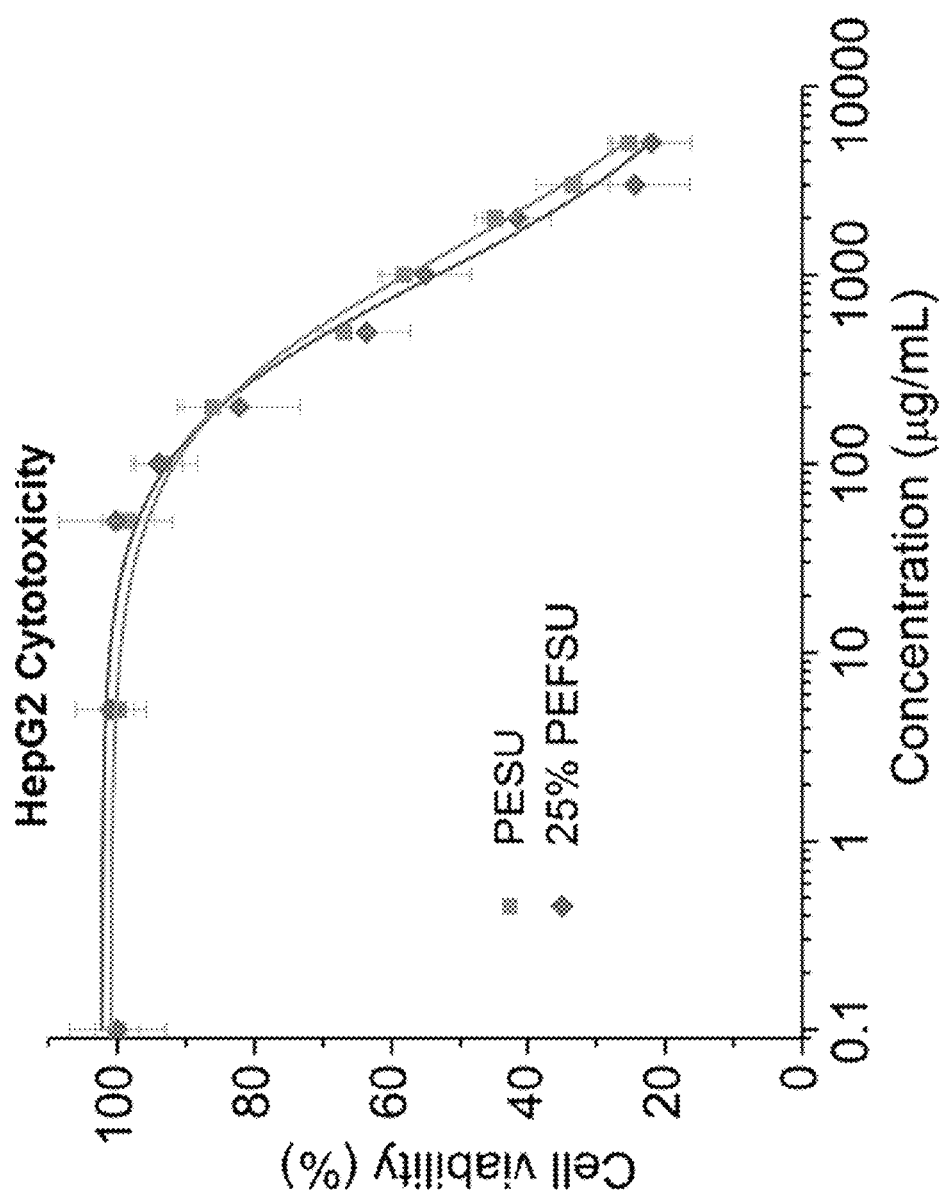
FIGS. 17A-17C: Effects of acNPs on cell viability and uptake into cells and the lysosomes.

The cytotoxicity of acNPs was determined in the HepG2 cell line. To determine the optimal acNPs (PESU and 25% PEFSU) concentration useful for treating HepG2 cells without inducing significant cell death, dose response cell cytotoxicity assays were done using various concentrations of acNPs ranging from 10 μg/mL to 1000 μg/mL for 24 hours. The percent of viable cells under different concentration treatment conditions are then normalized to the control, untreated cells with either palmitate or acNPs. The two types of acNPs did not result in significant cell death up to a concentration of 1000 μg/mL (FIG. 17A). An optimal dose was 100 μg/mL is selected for further assays to avoid any cytotoxicity to the cells.

acNPs Localized to the Lysosomes.

Figure 17B:
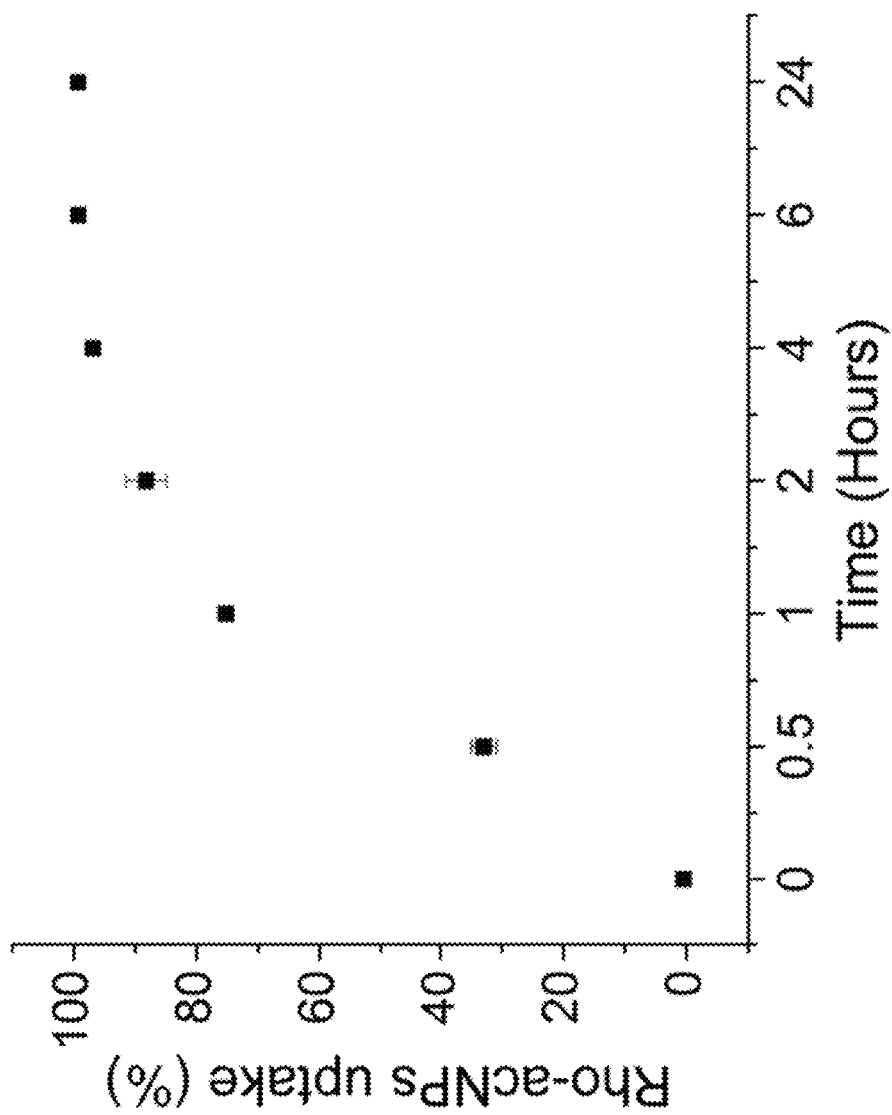
Figure 17C:
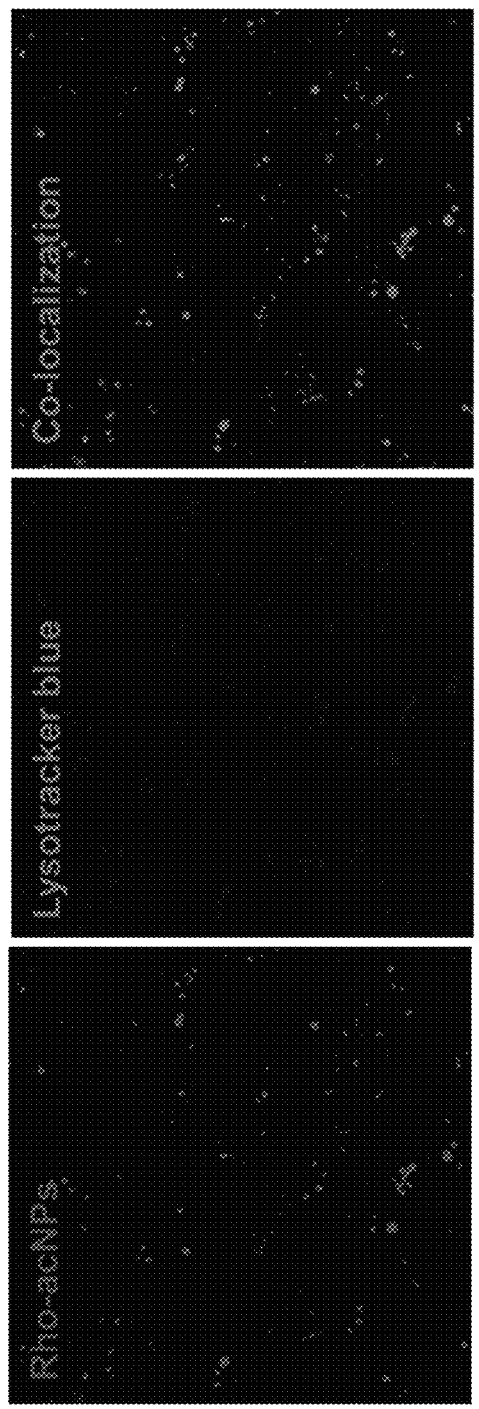

Timely uptake into hepatocytes and specific localization to lysosomes is important for the acNPs to exert their effect in vitro. The size of the acNPs (~100 nm) was expected to lead to uptake and localization within the endosome-lysosome system. Using the selected concentration of 100 μg/mL, rhodamine labelled acNPs (Rho-acNPs) were incubated with HepG2 cells for 24 hours. Flow cytometry determined that most of the Rho-acNPs uptake occurred within the first 8 hours (FIG. 17B). Colocalization confocal microscopy with LysoSensor™ blue dye confirmed that Rho-acNPs localized into lysosomes in HepG2 cells (FIG. 17C).

10% PEFSU acNPs and 25% PEFSU acNPs Restores Lysosomal pH and Cell Viability in HepGs Cells Exposed to Fatty Acids The capability of acNPs to acidify dysfunctional lysosomes in hepatocytes and β-cells were quantified by monitoring the cells via confocal imaging using LysoSensor™ yellow/blue dye, which varies its emission based on pH. Cells were either incubated with 400 μM 4:1 palmitate complexed to bovine serum albumin (BSA) (4:1 palmitate:BSA) and co-incubated with different acNPs at different concentrations ranging from 0.1 to 1000 μg/mL for 16-18 hours (16 hours for HepG2 cells and 18 hours for B-cells). Cells with no added palmitate or acNPs along with cells treated only with acNPs were used as controls. The 18 hour time-point for palmitate:BSA treatment was selected for B-cells, compared to 20 or 24 hours, as this time-point resulted in the highest lysosomal pH alkalinization in cells (10). After treatment, 1 μM of LysoSensor™ yellow/blue dye was added and the cells were imaged within 5 minutes of dye addition to minimize alkalization. Ratio values were calibrated to lysosomal pH based on a previously determined standard curve (14). HepG2 cells treated with palmitate for 16 hours experienced a significant elevation of lysosomal pH (~0.6 pH units).

Figures 18A, 18B, 18C:
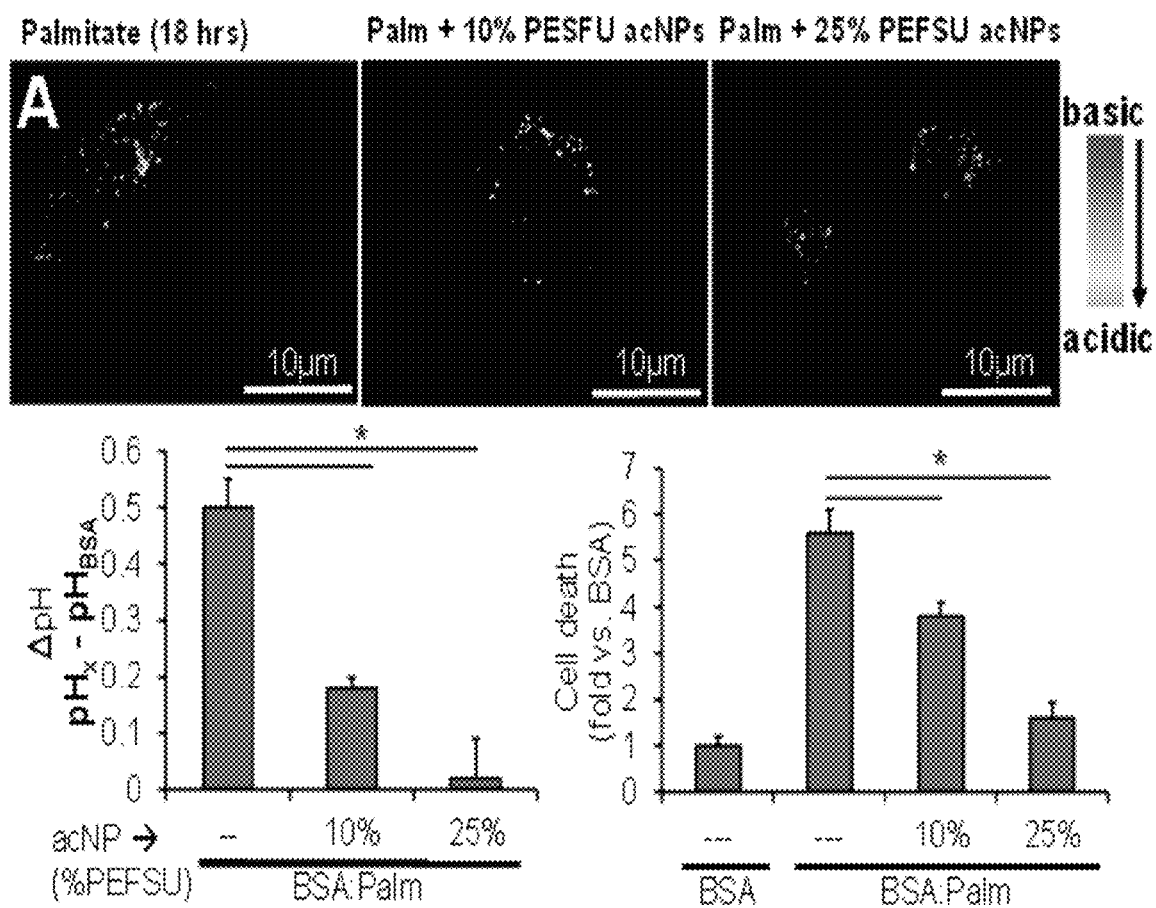
FIGS. 18A-18C show that acNPs improve lysosomal acidity and rescue cell death under lipotoxicity.

The results show that HepG2 cells treated with 4:1 palmitate:BSA co-incubated with or without acNPs composed of 10% PEFSU or 25% PEFSU (polyesters 1 and 4 respectively) exhibit a significant restoration of lysosomal pH, similar to the BSA control (FIGS. 18A and 18B).

The cells were assessed following palmitate-BSA (4:1 ratio) and various concentrations (0.1-1000 ug/mL) acNPs incubation for 24-72 hours. Preliminary data of HepG2 cells treated with palmitate-BSA and acNPs from 10% PEFSU or 25% PEFSU (polyesters 1 and 4 respectively) showed significant rescue of cell viability compared to untreated control (FIG. 18C).

acNPs Restores Lysosomal pH and Size in Hepatocytes Exposed to Palmitate.

Figure 19A:
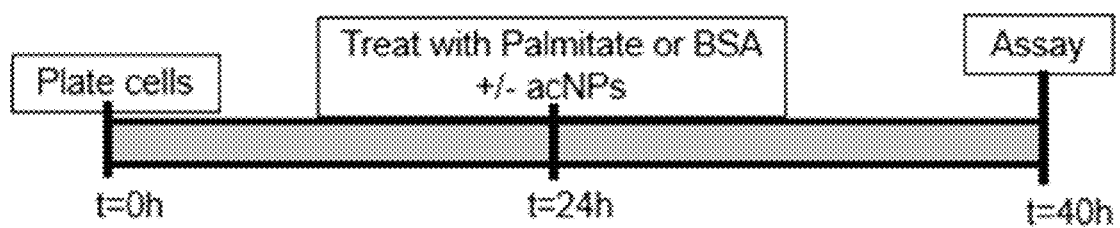
FIGS. 19A-19D shows the effects of acNPs on changes in lysosomal acidity and cathepsin L in cells treated with BSA (control) or Palmitate in the presence or absence of acNPs.

Having demonstrated acNPs function and cellular uptake into lysosomes, the essential question is whether acNPs could restore lysosomal acidity in cells exposed to LT. HepG2 cells were exposed to BSA, 0.4 mM palmitate complexed to BSA (Palm:BSA) with or without 25% PEFSU acNPs, (FIG. 19A). Following incubation, LysoSensor™ yellow/blue dye (ThermoFisher Scientific) was added at a 75 nM concentration, lysosomal acidity and size were assessed by confocal imaging, and image analysis was carried out with MetaMorph® within 5 minutes of dye addition to prevent lysosomal alkalization.

Figure 19B:
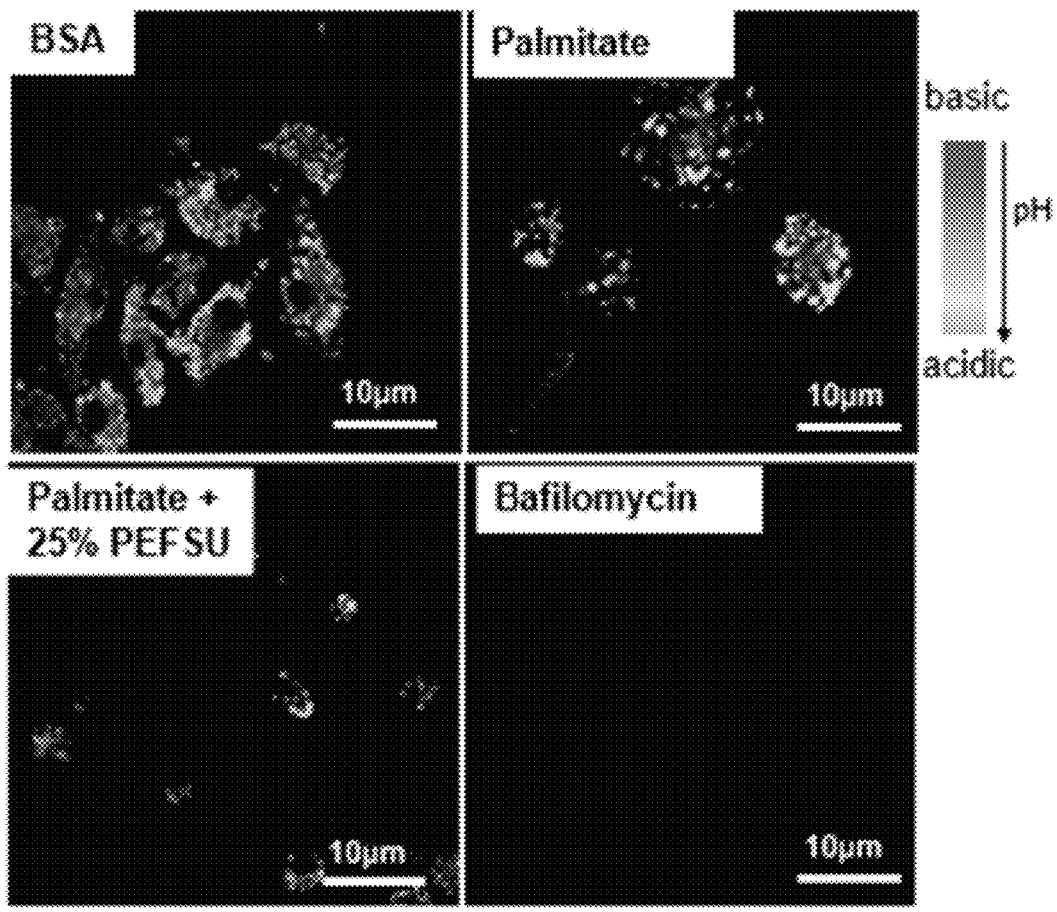
Figure 19C:
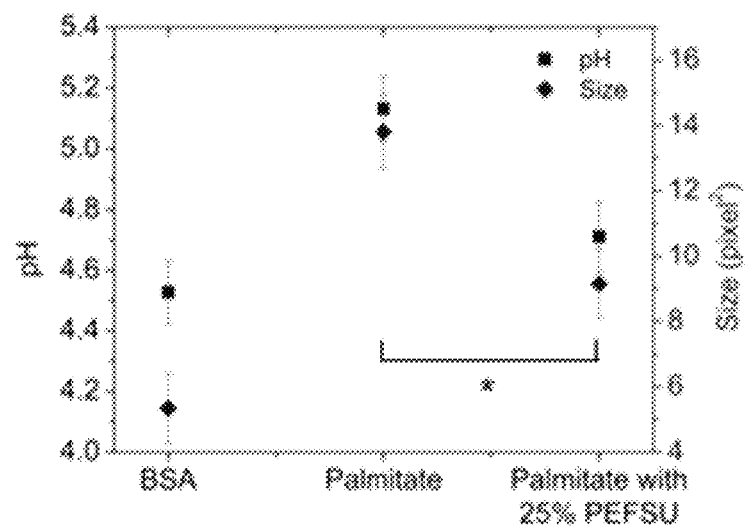

To demonstrate specificity of LysoSensor™ staining of lysosomes, cells were treated with 100 μM bafilomycin for 2 h before imaging, which showed no LysoSensor™ staining because of neutralization of lysosomal pH. (FIG. 19B). FIG. 19C shows that palmitate exposure significantly increased lysosomal pH (□), by a magnitude of 0.6 pH units. Exposure to palmitate also increased the lysosomal size (◇) compared to BSA-treated cells. Treatment with PESU acNPs did not induce a reduction of pH, consistent with FIG. 14B, which indicates a slow rate of degradation and acid release. On the other hand, treatment with 25% PEFSU acNPs caused a decrease of 0.3 and 0.5 pH units in HepG2 cells respectively (FIG. 19C). Addition of 25% PEFSU acNPs also caused a significant reduction in average lysosomal size, probably due to increased turnover of lysosomes via autophagy.[34]

Figure 20:
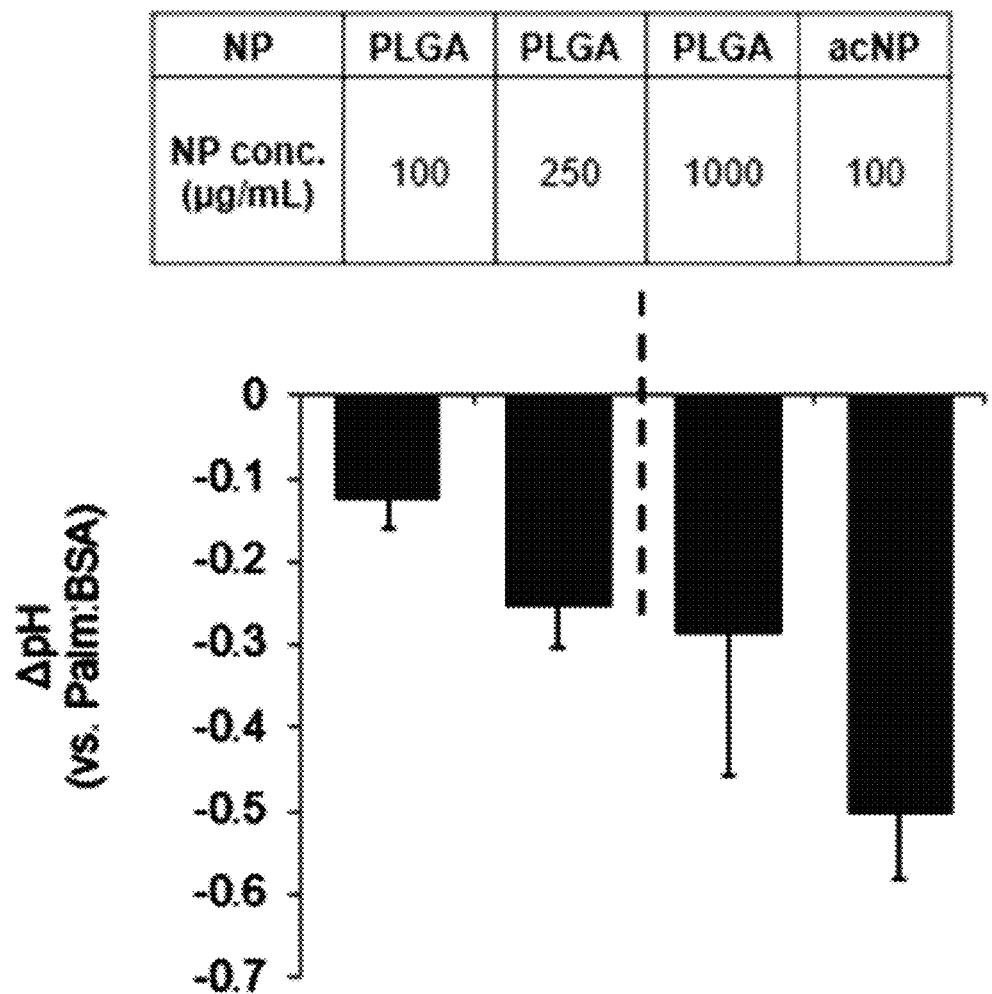
FIG. 20 shows lysosomal pH changes of 25% PEFSU acNPs and PLGA NPs in HepG2 cells compared to palmitate control. acNPs at 100 ug/mL was able to generate higher lysosomal pH changes than 1 mg/mL of PLGA NPs, showing a much stronger acidification effect.

Treatment with PLGA nanoparticles, which have been previously shown to acidify lysosomes when used at a concentration of 1 mg/ml[39], partially restored lysosomal acidity under palmitate at a concentration of 1 mg/ml (FIG. 20). In comparison, 25% PEFSU acNPs restored lysosomal acidity at a 10-fold lower concentration of 100 μg/ml. The activity of lysosomal cathepsins is pH dependent, and studies have shown that exposure to fatty acids results in the inhibition of cathepsin activity.[16,34]

Figure 19D:
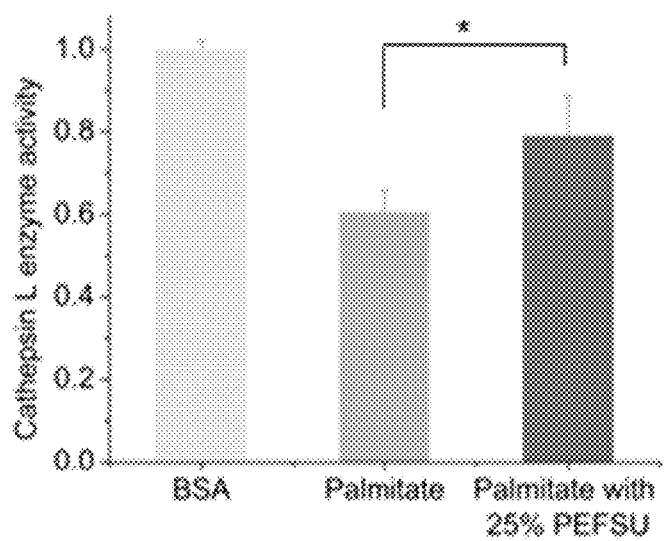

To determine if acNP restores lysosomal enzyme cathepsin L activity in palmitate incubated cells, Magic Red cathepsin L fluorescent substrate assay was carried out. Results showed that restoration of lysosomal acidity with 25% PEFSU acNPs significantly increased the pH-dependent activity of lysosomal cathepsin L. This increase in cathepsin L activity correlated with an increase in Magic Red fluorescence intensity (FIG. 19D) in acNP-treated palmitate-incubated cells compared to non-acNPs treated palmitate-incubated cells. This further confirms that the reduction of lysosomal acidity causes a functional rescue of lysosomes under lipotoxicity within 16 hrs.

Lysosomal Acidification Controlled by acNPs Restores Autophagic Flux in HepG2 Cells Exposed to Fatty Acids.

During autophagosome formation, phosphatidylethanolamine is conjugated to cytosolic LC3 (i.e., LC3-I) to form LC3-II, which is sequestered in autophagosome membranes. Thus, LC3-II accumulation serves as a surrogate marker for autophagosome accumulation. (see, FIG. 1). To investigate whether the restoration of lysosomal acidity relieved the inhibition of autophagic flux in HepG2 cells exposed to palmitate, the intracellular accumulation of microtubule associated protein 1A/1B light chain 3 (LC3-II) was measured. To further confirm the acNPs' effect on autophagic degradation, the levels of p62 protein, a protein that is degraded during autophagy and is used as a marker for autophagic flux was also measured.[44] To validate and determine the amount of time required for palmitate to cause an inhibition of autophagic flux in HepG2 cells, HepG2 cells were incubated with palmitate for either 16 hrs, 20 hrs or 24 hrs, and the expression levels of LC3II and p62 were analyzed using Western blot (data not shown for 20 and 24 hrs). At 16 hours, palmitate exposure increased LC3II and p62 levels indicating inhibition of autophagic flux and accumulation of autophagic substrate. (FIG. 21A). Incubation of the HepG2 cells with PBSU acNPs for 16 hours did not result in significant change in LC3II and p62 expression levels (Data not shown). Treatment with 25% PEFSU acNPs resulted in a significant reduction of LC3II levels, indicating clearance of autophagosomes (FIGS. 21A-21C). 25% PEFSU acNPs also significantly lowered p62 levels.

FIG. 22A shows that 10% PEFSU localized and restored cathepsin L activity as well as 25% PEFSU in HepG2 cells with chronic palmitate exposure. To further pinpoint the effect of autophagic flux restoration through increasing lysosomal acidity, the cells were treated with bafilomycin, a V-ATPase inhibitor that elevated lysosomal pH, for 2 hours. The LC3II and p62 levels increased significantly upon treatment. FIG. 22B indicates that acNPs increased autophagy because of decrease of lysosomal pH. On the other hand, cells treated with leupeptin, a lysosomal protease inhibitor that prevents degradation of autophagosomal contents upon fusion with lysosomes also showed increased levels of LC3II and p62 levels. The results showed that the restoration of autophagy by acNPs is dependent on the activity of lysosomal proteases. Degradation of the lysosomal enzymes resulted in increased acidity, which is important to lower lysosomal pH and hence increase autophagy.

Lysosomal Acidification Controlled by acNPs Reduces Lipid Droplets Accumulation.

Pharmacological inhibition of lysosomal acidification in vivo results in fatty liver and accumulation of lipid droplets within hepatocytes, which plays a causal role in the development of insulin resistance.

Figure 23A:
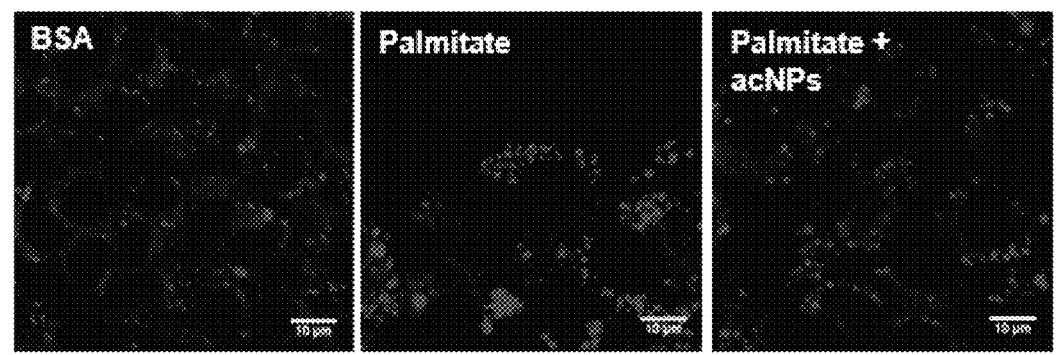
Figure 23A:
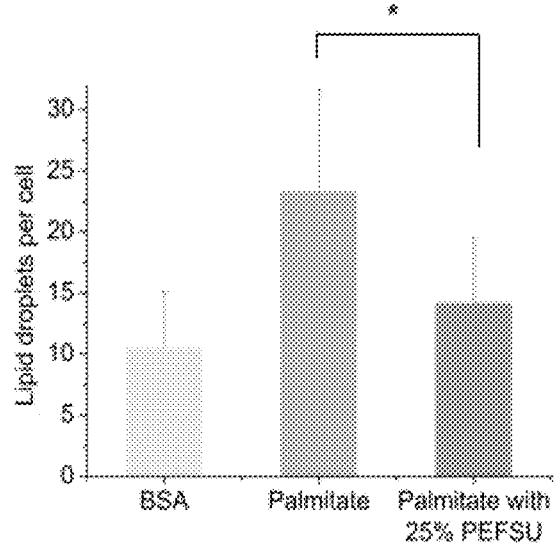
Figure 23A:
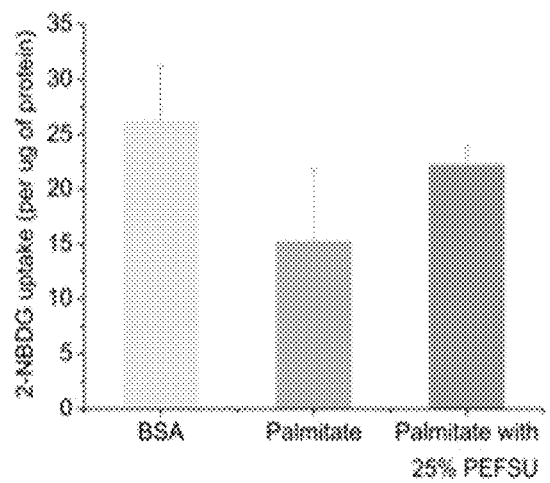

Because autophagy consumes lipid droplets (lipophagy), we hypothesize that activation of autophagy with acNPs will reduce the lipid burden on hepatocytes by increasing lipophagy. To measure lipid droplet content per cell, HepG2 cells were treated with palmitate with and without acNPs, and lipid droplets were visualized in live cells using Nile Red (ThermoFisher Scientific) staining. HepG2 cells under BSA conditions had a basal lipid droplet number of 10, while treatment with palmitate increased the number of lipid droplets significantly to about 20-25 per cell. Co-treatment of HepG2 cells with 25% PEFSU reduced the accumulation of lipid droplets to 15 per cell, indicating an increase in lipophagy and reversal of lipid accumulation (FIGS. 23A and 23B).

The capacity of insulin to reduce glucose production by hepatocytes is diminished in obese, insulin resistant humans and is strongly correlated to hepatic lipid accumulation.[47] To assess gluconeogenic capacity, hepatocytes were treated under various conditions as described. Next, they were acutely exposed to 2 mM sodium pyruvate and 20 mM lactate for 16 hours. Insulin inhibition of gluconeogenesis was measured by monitoring the media glucose levels (2NBDG) over 10 hours following treatment of hepatocytes with 10 nM insulin. Insulin inhibition of gluconeogenesis is measured by monitoring the media glucose levels over 3 hours following treatment of hepatocytes with 10 nM insulin. FIG. 23C shows 2-NBDG uptake, an analog of glucose. Addition of insulin inhibited gluconeogenesis through increasing glucose (2-NBDG) uptake. Palmitate addition decreased glucose uptake, and addition of acNPs increased glucose uptake and hence inhibition of gluconeogenesis.

acNPs Reduces Serum Triglyceride Levels in High Fat Diet Mice Model of NAFLD

Figure 24A:
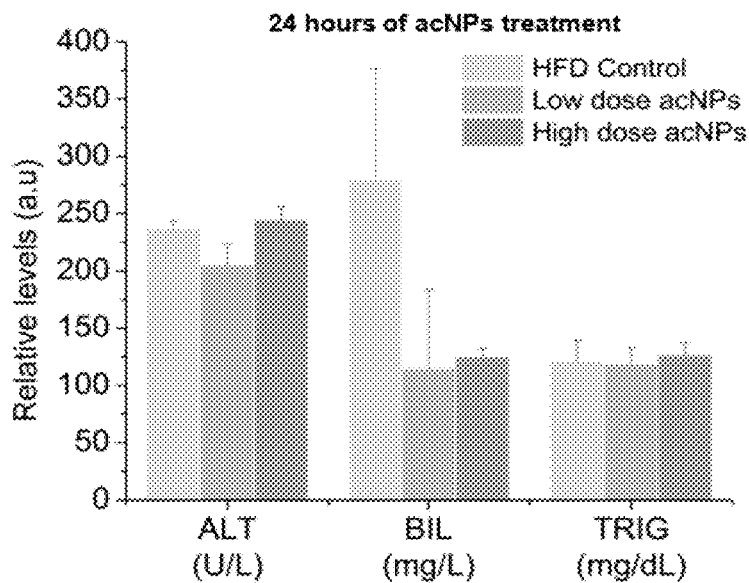
FIGS. 24A and 24B show the serum levels of alanine transaminase (ALT), bilirubin (BIL) and triglycerides (TRIG) after 24 hours and 6 days of acNPs treatment (low and high dose) on mice fed on 16 weeks of high fat diet, respectively. 6 days of acNPs treatment resulted in significant reduction in triglyceride level in the serum.
Figure 24B:
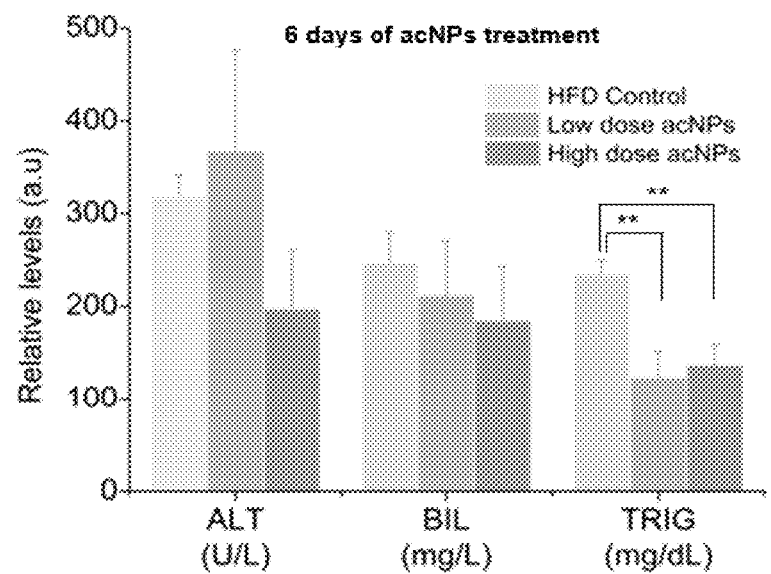

Having shown that acNPs of the present invention are functional in vitro, the toxicity and efficacy of acNPs was tested in a mouse model of NAFLD. C57BL/6J DIO mice (Jackson Laboratory) fed with a high fat diet (HFD) (D12492: 60% kcal energy as fat, Research Diets, Inc) for 16 weeks as the in vivo model of NAFLD. HFD mice subjected to a single intravenous injection of a sterile saline solution containing either 100 mg/kg/day of acNPs (low dose) or 300 mg/kg/day acNPs (high dose) for either one day or every other day for six days. At the end of each treatment, the mice were sacrificed, and serum tested for changes in alanine amino transferase (ALT) and bilirubin (BIL) levels as well as the triglyceride (TRIG) levels. ALT and BIL serum levels in serum are indicative of liver damage. Addition of either low or high doses of acNPs at day 1 (24 h) or day 6 did not significantly change the serum ALT and BIL levels compared to HFD control. However, the serum triglyceride levels decreased significantly with the addition of acNPs at either a low dose or high dose after six days of treatment (FIGS. 24A and 24B).

acNPs Reduces Lipid Droplets Levels in High Fat Diet Mice Model of NAFLD

Figure 25:
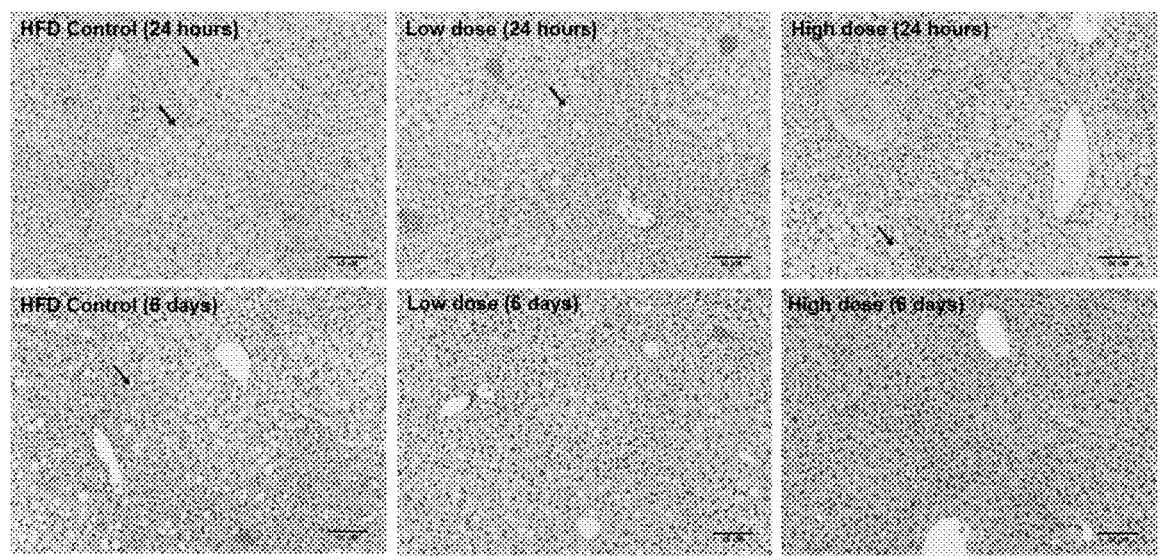
FIG. 25: H & E stains of liver sections of 16 weeks high fat diet mice treated with low and high dose acNPs for either 24 hours or 6 days. The degree of steatosis, fibrosis, and inflammation were characterized from the H & E stains. In HFD control mice, the liver section shows significant areas of enlarged hepatocytes, and lipid droplets accumulation, while mice under low dose or high dose acNPs for 6 days show significant reduction in lipid droplets accumulation.

Representative mouse liver tissue sections were obtained, and the amount of lipid droplet accumulation (steatosis) was assessed using H & E trichrome staining (FIG. 25). In HFD control, the liver section showed significant areas of enlarged hepatocytes, and lipid droplets accumulation. Treatment with low dose acNPs or high dose acNPs for 6 days show significant reduction in lipid droplets accumulation (FIG. 25).

In summary, to modulate or control the rate and degree of acid release, we synthesized different polyesters by varying either the chain length of the diol, or increasing the ratio of tetrafluorosuccinic acid to succinic acid. Different nanoparticles were also synthesized and characterized based on these newly synthesized polymers. We have found that increasing the length of diol decreases the rate of acid release, while increasing the amount of tetrafluorosuccinic acid to succinic acid increases the amount of acid released. Briefly, ethylene glycol-based nanoparticles (PEFSU) showed the highest rate of acid release and degradation, while butylene glycol-based nanoparticles had the slowest rate. The parameters to make the nanoparticles also have a strong association with polymer properties. Nanoparticles based on different polyesters were assessed for their cytotoxicity and acid restoration degree in lysosomes to develop in vivo therapeutic strategies for different treatment regimes for lysosomal pH dysfunctional diseases.

Materials and Methods acNPs Polymers Synthesis and Characterization

Di-acid monomers tetrafluorosuccinic acid (Matrix Scientific), succinic acid (Sigma Aldrich) were added at varying ratios in a round bottom flask. Ethylene glycol (Sigma Aldrich) were added at a 5 or 10 mol % excess, together with metal catalyst titanium isoproxide (TIPT) (Sigma Aldrich), and distilled azetropically at 120° C. for 16 hours. Subsequently, a vacuum was slowly applied to prevent excessive foaming, minimize oligomer sublimation, removing excess water, and further condensation to form higher molecular weight polymer chains. The temperature was increased to 130-140° C. for at least 12 hours. The reaction was stopped, and the final product precipitated in cold diethyl ether and dried under high vacuum for further storage and use.

Polymers Characterization (NMR and GPC)

$^1H$, $^{13}C$, and $^{19}F$ NMR spectra were recorded on an Agilent 500 MHz VNMRS spectrometer. $CDCl_3$ was used as solvent. Nuclear magnetic resonance (NMR) chemical shifts for the different polymers were determined:

$^1H$ NMR [(500 MHz, $CDCl_3$): PESU 2.66 (s, 1H), 4.29 (s, 1H)], [25% PEFSU 2.66 (s, 1H), 4.29 (s, 0.69H), 4.37 (s, 0.25H), 4.56 (s, 0.25H), 4.65 (s, 0.06H)]. $^{13}C$ NMR [(500 MHz, CDC13): PESU, 62.35, 76.76], [25% PEFSU 29.66, 61.37, 62.35, 65.37, 76.77, 107.89, 159.06]. $^{19}F$ NMR [(500 MHz, $CDCl_3$): 25% PEFSU −119.9, −120.6].

$^1H$ NMR [(500 MHz, $CDCl_3$): PBSU 1.58 (s, 1H), 1.70 (s, 2H), 2.62 (s, 2H), 4.11 (s, 2H)], [50% PBFSU 1.70 (m, 2H), 1.86 (m, 2H), 2.62 (s, 2H), 4.11 (m, 2H), 4.38 (m, 2H)], [100% PBFSU 1.86 (s, 1H), 4.39 (s, 1H)]. $^{13}C$ NMR [(500 MHz, $CDCl_3$): PBSU, 25.19, 28.99, 64.15, 77.28], [50% PBFSU 25.17, 28.95, 64.18, 67.52, 76.76, 107.98, 159.29], 100% PBFSU 24.48, 67.17, 76.74, 107.97]. $^{19}F$ NMR [(500 MHz, $CDCl_3$): 50% PBFSU −124.18, −121.40--119.28], 100% PBFSU −120.04.

Average molecular weights (Mn) and polydispersity (PDI) were measured on a gel permeation chromatography (GPC) equipped with a Waters 410 refractive index detector, a Waters 515 HPLC pump, and three UltraStyragel columns at 25° C. with THF as eluent at a flow rate of 1.0 mL/min. Monodisperse polystyrene standards were used as calibrations.

acNPs Nanoparticles Synthesis and Characterization

The acNPs were formed from the acNPs polymers using nanoprecipitation. Briefly, 5-8 mg of either PESU or 25% PEFSU or PBFSU polymer was dissolved in 0.5-0.6 mL of dimethylformamide (DMF) (Sigma Aldrich) and filtered through a 0.2 µm syringe filter (Millipore) to remove large aggregates or dust. A surfactant (30-32 mg) of sodium dodecyl sulfate (SDS) (Sigma Aldrich) was dissolved in 2-4 mL nanopore water (Millipore, endotoxin free), and stirred at high speeds of 1 k-1.7 k or 1 k-1.3 k rpm. The solution of polymer in DMF was then added drop wise into the fast stirring aqueous solution. Immediately after, the emulsion was placed into SnakeSkin dialysis tubing (MWCO 10 KDa) and dialyzed against nanopore water for 6-24 h. For Dynamic Light Scattering (DLS) measurements, 200 uL of the solution was diluted in 2.8 mL of DI water, and the size and zeta potential were obtained from the Brookehaven dynamic light scattering instrument. All measurements were performed in triplicate (n=3).

Scanning Electron Microscopy acNPs were diluted 100 times in DI water. Aliquots were plated on silicon wafers and allowed to air dry overnight. The wafers were affixed to aluminum stubs with copper tape and sputter coated with 5 nm Au/Pd. These samples were imaged using a Supra 55VP field emission scanning electron microscope (ZEISS) with an accelerating voltage of 2 kV and working distance of 5.5 cm or 6.0 cm. Gel permeation chromatography The molecular weight distribution (MWD) was measured at 30° C. with SEC (Agilent 1200 SEC) equipped with an Agilent-DRI refractive index detector and three columns: a PL gel 10 µm guard column and two PL gel Mixed-D 10 µm columns (linear columns of MWPS ranging from 500 to $10^6$ g/mol). Tetrahydrofuran was used as a solvent. The concentration of sample solution was about 1 mg/mL, and the flow rate of the eluent was of 1 mL/min. Polystyrene standards were used for calibration.

Differential Scanning Calorimetry and Thermogravimetric Analysis (DSC & TGA)

The thermal transitions were recorded with DSC on a Q200 thermal analyzer (TA Instruments) with a standard heating-cooling-heating mode. The heating rate was 10° C./min and cooling rate was 5° C./min. The thermal decomposition behavior was recorded with TGA (Q500, TA Instruments). The samples were heated from room temperature to 600 at 20° C./min under $N_2$ atmosphere.

Degradation Assays

Degradation assays were carried out for the butylene-based series of polyesters. First, acNPs from the butylene series were prepared, and suspended either in water or serum and incubated in 37° C. over time. At specific time points, the solutions containing acNPs were centrifuged, the pellet dried in $N_2$ atmosphere overnight, and re-dissolved in THF solvent for analysis using GPC.

Cell Culture and Cytotoxicity

HepG2 cells were cultured in DMEM media supplemented with 10% FBS, 1 mM glutamine, 50 units/ml penicillin, and 50 g/ml streptomycin. In some studies, primary hepatocytes were obtained from ATCC and maintained in DMEM media supplemented with 10% FBS, 1 mM glutamine, 50 units/ml penicillin, and 50 g/ml streptomycin. The cytotoxicity of acNPs was evaluated using an MTS cell proliferation assay (Abcam). HepG2 or primary hepatocytes were cultured in a 96-well plate at 15000 cells/well for 1 day, after which the media was exchanged for media containing either no treatment or 0, 50, 250, 500 or 1000 µg/mL of acNPs. The cells were then incubated with treatment for 24 hours, after which cell viability was quantified relative to the no treatment (control), after correcting for background absorbance. Three wells per treatment concentration were used, and the assay was repeated three times.

Palmitate: BSA Preparation

Palmitate was dissolved in DMSO (Millipore). This solution was dissolved at 45° C. in MEM media containing 6.7% fatty acid-free BSA (EMD Millipore) to make a 4 mM (10×) stock. For control BSA conditions, a 10× stock of MEM media containing 5% BSA and 1% DMSO was used. For the treatment conditions, the 10× stocks were added to MEM media containing 1% FBS, 50 U/ml penicillin, and 50 g/ml streptomycin and glucose at 10 mM. The pH of the treatment media were then adjusted to 7.4, followed by sterile filtration before treating the HepG2 cells for 16 h with palmitate with and without acNPs.

Flow Cytometry

FACS analyses of rhodamine-labelled acNP-treated cells was carried out using a 620 FACScan. FACS data analysis was performed using FACScalibur (Beckman Coulter). The cells were trypsinized, washed twice with PBS by centrifugation, and then subjected to flow cytometry. Cell debris was excluded by gating on the forward and side scatter plot.

LysoSensor™ Staining and Image Analysis

For co-localization imaging, cells were first incubated with Rho-acNPs for 24 hours and LysoSensor™ blue, DND-22 dye, was added according to manufacturer's protocol for 2 hours. The cells were then replaced with fresh media and imaged using confocal microscopy to determine the amount of rhodamine and Lysosensor blue signal overlap. For lysosomal pH determination, cells were stained with 1 µM LysoSensor™ yellow/blue for 5 min followed by confocal imaging using a 360 nm excitation and collecting images at the yellow wavelength range (510-641 nm) and at the range of blue wavelength (404-456 nm). The ratio between yellow and blue was calculated using MetaMorph software. In brief, background noise was removed by a median filter, followed by thresholding to identify individual lysosomes. Mean yellow and blue fluorescence intensities were obtained for the identified lysosomes, and yellow/blue ratio values were calculated. Quantification of pH changes was achieved by imaging LysoSensor™ fluorescence in 2-(N-morpholino) ethanesulfonic acid buffer of varying pH and establishing a standard curve of LysoSensor™ fluorescence ratio to pH. In the cases where ΔpH values are shown, a separate standard curve was not obtained but changes in LysoSensor™ ratio were converted to ΔpH by using previous standard curve equations, allowing relative pH changes to be calculated but not absolute pH values. For representative images shown, ratio images were generated by dividing yellow and blue LysoSensor™ images, and contrast was adjusted identically on all images to improve visualization. Pseudocoloring was applied to increase resolution of LysoSensor™ ratio changes.

Magic Red Cathepsin L Activity Assay

Cells were stained with 10 µg/ml Magic Red cathepsin L (MR-cathepsin L; Immunochemistry Technologies) for 1 h. The cells were washed three times with PBS and imaged using Celigo Imaging Cell Cytometer (Brooks Life Science Systems). A red (531/40 excitation; 629/53 emission) fluorescence channel was imaged for each well. Analysis parameters for images acquired by Celigo Imaging Cell Cytometer were optimized to identify individual cells based on fluorescence. Mean fluorescence intensity per cell values were determined by the mean integrated intensity per cell values to exclude error from background pixels included in identified cell regions. At least 1,000 cells were analyzed per well, with three- to four-well replicates per experiment.

Western Blot

Samples were prepared as described in Trudeau, et al.[2] The samples were loaded on a 4-12% polyacrylamide gel (Invitrogen) and transferred onto a polyvinylidene difluoride membrane (Invitrogen) using a wet (tank) transfer machine. LC3 (Cell Signaling), GAPDH (Cell Signaling), and p62 (Cell Signaling) antibodies were used according to the manufacturer's instructions.

Glucose Production in Hepatocytes

Glucose production assays were carried out as described in Herzig, et al.[3] Briefly, cells were cultured, and incubated under different treatment conditions. The cell medium was then switched to glucose- and phenol-free DMEM (pH 7.4) supplemented with 20 mM sodium lactate and 2 mM sodium pyruvate for 16 hours. 10 nM insulin was added 3 hours before the end of treatment, and 2-NBDG was added 10 minutes before the end of treatment. Glucose content was measured using a glucose uptake assay kit (Cayman Chemicals).

Statistics

Predetermined statistical methods were used to determine the significance of the study results. Cytotoxicity, lysosomal pH and size, autophagic flux, protein expression levels, lipid count/cell etc. were expressed as mean±S.D. Statistical analysis were performed using Origin Lab Pro 8.5 software; two-sided P values<0.05 considered statistically significant.

It is understood that the examples and embodiments described herein are for illustrative purposes only and that various modifications or changes in light thereof will be apparent to persons skilled in the art and are to be included within the spirit and purview of this application and scope of the appended claims. The scope of the invention should, therefore, be determined not only with reference to the above description, but, should instead be determined with reference to the appended claims, along with the full scope of equivalents to which such claims are entitled. All publications, patents, and patent applications cited herein are hereby incorporated by reference in their entirety for all purposes.

What is claimed is:

1. An acid-releasing fluorinated polyester nanoparticle (acNP) comprising:
(i) a polyester and (ii) a tetrafluorosuccinic acid (TFSA), wherein the nanoparticle releases an acid when exposed to an environment having a pH of about pH 6.0.

2. The nanoparticle of claim 1, wherein the nanoparticle does not substantially release an acid at pH about pH 7.0.

3. The nanoparticle of claim 2, wherein the nanoparticle further comprises succinic acid (SA).

4. The nanoparticle of claim 3, wherein the ratio of TFSA to SA ranges from 100:0 (TFSA:SA) to 10:90 (TFSA:SA).

5. The nanoparticle of claim 3, wherein the ratio of TFSA to SA comprises a ratio having at least about 10:90, about 15:85, about 20:80, about 25:75, about 30:70, about 35:65, about 40:60, about 45:55, about 50:50, about 55:45, about 60:40, about 65:35, about 70:30, about 75:25, about 80:20, about 15:15, about 90:10, about 95:5, or about 100:0.

6. The nanoparticle of claim 5, wherein the nanoparticle comprises a polyester comprising a diol having at least an ethylene glycol, a propylene glycol, or a butylene glycol.

7. The nanoparticle of claim 6, wherein the nanoparticle comprises a polyester of at least an ethylene glycol, and a TFSA.

8. The nanoparticle of claim 6, wherein the nanoparticle comprises a polyester of at least a propylene glycol, and a TFSA.

9. The nanoparticle of claim 6, wherein the nanoparticle comprises a polyester of at least a butylene glycol, and a TFSA.

10. The nanoparticle of claim 6, wherein the nanoparticle comprises at least a polyester and a TFSA having at least 10% PEFSU (ethylene glycol and TFSA); 15% PEFSU, 20% PEFSU, 25% PEFSU, 30% PEFSU, 35% PEFSU, 40% PEFSU, 45% PEFSU; 50% PEFSU; 55% PEFSU, 60% PEFSU, 65% PEFSU, 70% PEFSU, 75% PEFSU, 80% PEFSU, 85% PEFSU, 90% PEFSU, 95% PEFSU, 100% PEFSU, 10% PPFSU (propylene glycol and TFSA); 15% PPFSU, 20% PPFSU, 25% PPFSU, 30% PPFSU, 35% PPFSU, 40% PPFSU, 45% PPFSU; 50% PPFSU; 55% PPFSU, 60% PPFSU, 65% PPFSU, 70% PPFSU, 75% PPFSU, 80% PPFSU, 85% PPFSU, 90% PPFSU, 95% PPFSU, 100% PPFSU, 10% PBFSU (butylene glycol and TFSA); 15% PBFSU, 20% PBFSU, 25% PBFSU, 30% PBFSU, 35% PBFSU, 40% PBFSU, 45% PBFSU; 50% PBFSU; 55% PBFSU, 60% PBFSU, 65% PBFSU, 70% PBFSU, 75% PBFSU, 80% PBFSU, 85% PBFSU, 90% PBFSU, 95% PBFSU, or 100% PBFSU.

11. The nanoparticle of claim 10, wherein the nanoparticle comprises at least one of 10% PEFSU, 15% PEFSU, 20% PEFSU, or 25% PEFSU.

12. The nanoparticle of claim 10, wherein the nanoparticle comprises at least one of 25% PPFSU, 50% PPFSU, 75% PPFSU, or 100% PPFSU.

13. The nanoparticle of claim 10, wherein the nanoparticle comprises at least one of 30% PBFSU, 50% PBFSU, 75% PBFSU, or 100% PBFSU.

14. The nanoparticle of claim 1, wherein the nanoparticle has an average diameter ranging from about 25 nm-50 nm, or from about 50 nm about 150 nm, or from about 150 nm-200 nm.

15. The nanoparticle of claim 14, wherein the nanoparticle has an average diameter less than about 100 nm.

16. The nanoparticle of claim 14, wherein a population of the nanoparticles has a PDI (polydispersity index) of less than 0.2 to about 0.14.

17. The nanoparticle of claim 14, wherein the nanoparticle has a size and a zeta potential that results in uptake into lysosomes via the endocytic pathway when the nanoparticle is contacted to a cell.

18. The nanoparticle of claim 17, wherein the nanoparticle or a plurality of the nanoparticle(s), when taken up by a cell, is effective to restore autophagic flux in the cell under conditions that impair lysosomal acidification.

19. The nanoparticle of claim 18, wherein the nanoparticle or a plurality of the nanoparticle(s), when taken up by a cell, is effective to enhance lysosome-autophagosome fusion capacity in the cell.

20. The nanoparticle of claim 19, wherein the nanoparticle or a plurality of the nanoparticle(s) is effective to induce a short and/or a long term recovery of lysosomal function in hepatocytes exposed to fatty acids, or in B-cells exposed to fatty acids.

21. The nanoparticle of claim 20, wherein the nanoparticle or a population of the nanoparticle(s) is effective to normalize hepatocyte lipid content.

22. The nanoparticle of claim 20, wherein the nanoparticle or a population of the nanoparticle(s) is effective to enhance B cell capacity to secrete insulin in response to glucose.

23. A pharmaceutical formulation comprising:
a plurality of acid-releasing fluorinated polyester nanoparticles further comprising (i) a polyester having at least an ethylene glycol, a propylene glycol, or a butylene glycol, and (ii) tetrafluorosuccinic acid; and
a pharmaceutically acceptable carrier.

24. The pharmaceutical formulation of claim 23, wherein the pharmaceutical formulation comprises a unit dosage formulation.

25. The pharmaceutical formulation of claim 23, wherein the formulation is substantially sterile.

26. The pharmaceutical formulation of claim 23, wherein the pharmaceutical formulation is formulated for administration orally, isophorectically, transdermally, parentally, intravenously, rectally, by aerosol, and by inhalation.

27. A method of promoting autophagy in cells of a mammal comprising:
contacting the cells with a plurality of acid-releasing fluorinated polyester nanoparticles,
wherein the acid-releasing fluorinated polyester nanoparticles comprise (i) a polyester having at least an ethylene glycol, a propylene glycol, or a butylene glycol, and (ii) a tetrafluorosuccinic acid (TFSA); and
wherein the nanoparticles release an acid when exposed to an environment having a pH of about 6.0.

28. The method of claim 27, wherein the method comprises administering to the mammal an effective amount of a pharmaceutical formulation comprising the acid releasing fluorinated polyester nanoparticles and a pharmaceutically acceptable carrier.

29. A method of treating a disease state in a mammal to restore lysosomal function, comprising:
administering to the mammal an effective amount of the acid-releasing fluorinated polyester nanoparticles comprising
(i) a polyester having at least an ethylene glycol, a propylene glycol, or a butylene glycol; and
(ii) a tetrafluorosuccinic acid (TFSA), or a pharmaceutical formulation thereof.

30. The method of claim 29, wherein the disease state is associated with impaired lysosomal acidity.

31. The method of claim 30, wherein the disease state associated with impaired lysoseomal acidity is selected from obesity, metabolic syndrome, type 2 diabetes (T2D), non-alcoholic fatty liver disease (NAFLD), and a neurodegenerative pathology.

32. The method of claim 31, wherein the disease state comprises a neurodegenerative pathology selected from an age-related dementia, Parkinson's disease, and Alzheimer's disease.

33. The method of claim 27 or 29, wherein the method is effective to restore autophagic flux under conditions that impair lysosomal acidification.

34. The method of claim 27 or 29, wherein the method is effective to enhance lysosome-autophagosome fusion capacity.

35. The method of claim 27 or 29, wherein the method is effective to enhance lysosomal hydrolase activity.

36. The method of claim 27 or 29, wherein the method is effective to produce short-term or long-term recovery of lysosomal function.

37. The method of claim 27 or 29, wherein the method is effective to produce short-term or long-term recovery of lysosomal function in hepatocytes exposed to fatty acids.

38. The method of claim 37, wherein the method is effective to normalize lipid content in the hepatocytes.

39. The method of claim 27 or 29, wherein the method is effective to produce short-term or long-term recovery of lysosomal function in B-cells exposed to fatty acids.

40. The method of claim 39, wherein the method is effective to enhance B-cell capacity to secrete insulin in response to glucose.

41. The method of claim 27 or 29, wherein the mammal is a human.

42. The method of claim 27 or 29, wherein the mammal is a non-human mammal.

43. The method for treating a mammal in need of liver transplantation, the method comprising perfusing the liver to be transplanted an effective amount of an acid-releasing fluorinated polyester nanoparticle comprising
   (i) a polyester having at least an ethylene glycol, a propylene glycol, or butylene glycol, and
   (ii) a tetrafluorosuccinic acid (TFSA); or a pharmaceutical formulation thereof.

44. The method for treating a mammal in need of liver transplantation, the method comprising de-lipidizing the liver to be transplanted an effective amount of an acid-releasing fluorinated polyester nanoparticle comprising
   (i) a polyester having at least an ethylene glycol, a propylene glycol, or butylene glycol, and
   (ii) a tetrafluorosuccinic acid (TFSA); or a pharmaceutical formulation thereof.

45. The method of claim 27 or 29, wherein the acid-releasing fluorinated polyester nanoparticles further comprise succinic acid (SA).

46. The method of claim 27 or 29, wherein the ratio of TFSA to SA ranges from 100:0 (TFSA:SA) to 10:90 (TFSA:SA).

47. The method of claim 27 or 29, wherein the acid-releasing fluorinated polyester nanoparticles comprise a diol having at least an ethylene glycol, a propylene glycol, or a butylene glycol.

* * * * *